United States Patent
Pelletier et al.

(10) Patent No.: US 9,228,940 B2
(45) Date of Patent: Jan. 5, 2016

(54) SYSTEMS, METHODS, AND APPARATUSES FOR IN SITU MONITORING OF CEMENT FLUID COMPOSITIONS AND SETTING PROCESSES THEREOF

(75) Inventors: Michael T. Pelletier, Houston, TX (US); Christopher Michael Jones, Houston, TX (US); B. Raghava Reddy, Houston, TX (US); Ashok K. Santra, The Woodlands, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 624 days.

(21) Appl. No.: 13/615,744

(22) Filed: Sep. 14, 2012

(65) Prior Publication Data
US 2014/0076551 A1    Mar. 20, 2014

(51) Int. Cl.

| | |
|---|---|
| E21B 47/005 | (2012.01) |
| G01N 21/47 | (2006.01) |
| E21B 33/03 | (2006.01) |
| E21B 33/13 | (2006.01) |
| E21B 43/10 | (2006.01) |
| E21B 47/00 | (2012.01) |
| G01N 33/28 | (2006.01) |
| G01N 33/38 | (2006.01) |
| G01N 21/85 | (2006.01) |
| C04B 40/00 | (2006.01) |
| C09K 8/46 | (2006.01) |

(Continued)

(52) U.S. Cl.
CPC ............ *G01N 21/47* (2013.01); *C04B 40/0032* (2013.01); *C09K 8/46* (2013.01); *E21B 33/03* (2013.01); *E21B 33/13* (2013.01); *E21B 43/10* (2013.01); *E21B 47/0005* (2013.01); *G01N 21/85* (2013.01); *G01N 33/2823* (2013.01); *G01N 33/383* (2013.01); *G01N 21/64* (2013.01); *G01N 21/65* (2013.01)

(58) Field of Classification Search
CPC ..... E21B 47/0005; E21B 33/03; E21B 33/13; E21B 43/10; G01N 33/2823; G01N 21/47; G01N 21/64; G01N 21/65; G01N 33/383; C04B 40/0032; C04B 28/02
See application file for complete search history.

(56) References Cited

U.S. PATENT DOCUMENTS

| | | |
|---|---|---|
| 4,618,939 A | 10/1986 | Davis |
| 5,027,267 A | 6/1991 | Pitts et al. |

(Continued)

FOREIGN PATENT DOCUMENTS

| | | |
|---|---|---|
| EP | 2466063 A1 | 6/2012 |
| WO | 2014042867 A1 | 3/2014 |

OTHER PUBLICATIONS

International Search Report and Written Opinion for PCT/US2013/056814 dated Feb. 14, 2014.

(Continued)

*Primary Examiner* — Daniel P Stephenson
(74) *Attorney, Agent, or Firm* — McDermott Will & Emery LLP; John W. Wustenberg

(57) ABSTRACT

Optical analysis systems, methods, and apparatuses for analyzing fluids may be useful for in situ monitoring fluids that relate to cementing operations. For example, a method may include containing a cement fluid composition in a flow path comprising a wellbore; and optically interacting the cement fluid composition with an integrated computational element, thereby generating an output signal corresponding to a characteristic of the cement fluid composition, the integrated computational element being coupled to a tool.

17 Claims, 9 Drawing Sheets

(51) Int. Cl.
G01N 21/64 (2006.01)
G01N 21/65 (2006.01)

(56) References Cited

U.S. PATENT DOCUMENTS

| | | | |
|---|---|---|---|
| 5,400,137 A | 3/1995 | Winslow et al. | |
| 5,418,614 A | 5/1995 | Brost et al. | |
| 5,489,977 A | 2/1996 | Winslow et al. | |
| 6,198,531 B1 | 3/2001 | Myrick et al. | |
| 6,488,088 B1 | 12/2002 | Kohli et al. | |
| 6,529,276 B1 | 3/2003 | Myrick | |
| 6,532,839 B1* | 3/2003 | Kluth et al. | 73/866.5 |
| 6,561,488 B1* | 5/2003 | Walker | 254/134.4 |
| 6,634,425 B2* | 10/2003 | King et al. | 166/253.1 |
| 7,123,844 B2 | 10/2006 | Myrick | |
| 7,138,156 B1 | 11/2006 | Myrick et al. | |
| 7,472,748 B2 | 1/2009 | Gdanski et al. | |
| 7,623,233 B2 | 11/2009 | Freese et al. | |
| 7,697,141 B2 | 4/2010 | Jones et al. | |
| 7,712,527 B2 | 5/2010 | Roddy | |
| 7,834,999 B2 | 11/2010 | Myrick et al. | |
| 7,911,605 B2 | 3/2011 | Myrick et al. | |
| 7,920,258 B2 | 4/2011 | Myrick et al. | |
| 7,938,175 B2 | 5/2011 | Skinner et al. | |
| 8,049,881 B2 | 11/2011 | Myrick et al. | |
| 8,141,633 B2 | 3/2012 | Hampton et al. | |
| 2004/0060697 A1* | 4/2004 | Tilton et al. | 166/253.1 |
| 2007/0282647 A1 | 12/2007 | Freese et al. | |
| 2008/0231849 A1 | 9/2008 | Myrick et al. | |
| 2008/0276687 A1 | 11/2008 | Myrick et al. | |
| 2009/0073433 A1 | 3/2009 | Myrick et al. | |
| 2009/0097024 A1 | 4/2009 | Blackburn et al. | |
| 2009/0140144 A1 | 6/2009 | Myrick et al. | |
| 2009/0182693 A1 | 7/2009 | Fulton et al. | |
| 2009/0216504 A1 | 8/2009 | Priore et al. | |
| 2009/0219171 A1 | 9/2009 | Vigneaux | |
| 2009/0219512 A1 | 9/2009 | Myrick et al. | |
| 2009/0219538 A1 | 9/2009 | Myrick et al. | |
| 2009/0219539 A1 | 9/2009 | Myrick et al. | |
| 2009/0250613 A1 | 10/2009 | Myrick et al. | |
| 2009/0299946 A1 | 12/2009 | Myrick et al. | |
| 2009/0316150 A1 | 12/2009 | Myrick et al. | |
| 2010/0050905 A1 | 3/2010 | Lewis et al. | |
| 2010/0051266 A1 | 3/2010 | Roddy et al. | |
| 2010/0051275 A1 | 3/2010 | Lewis et al. | |
| 2010/0073666 A1 | 3/2010 | Perkins et al. | |
| 2010/0141952 A1 | 6/2010 | Myrick et al. | |
| 2010/0149537 A1 | 6/2010 | Myrick et al. | |
| 2010/0153048 A1 | 6/2010 | Myrick et al. | |
| 2010/0182600 A1 | 7/2010 | Freese et al. | |
| 2010/0195105 A1 | 8/2010 | Myrick et al. | |
| 2010/0245096 A1 | 9/2010 | Jones et al. | |
| 2010/0265509 A1 | 10/2010 | Jones et al. | |
| 2010/0302539 A1 | 12/2010 | Myrick et al. | |
| 2010/0305741 A1 | 12/2010 | Myrick | |
| 2010/0328669 A1 | 12/2010 | Myrick et al. | |
| 2011/0199610 A1 | 8/2011 | Myrick et al. | |
| 2011/0308788 A1 | 12/2011 | Ravi et al. | |
| 2012/0205103 A1 | 8/2012 | Ravi et al. | |
| 2014/0076551 A1* | 3/2014 | Pelletier et al. | 166/253.1 |

OTHER PUBLICATIONS

Brost et al., "Optical Methods for Monitoring Treating Chemicals in Oilfield Water Systems," SPE 22781, 217-232, 1991.

Myrick, et al. "Spectral Tolerance Determination for Multivariate Optical Element Design," Fresenuis' Journal of Analytical Chemistry, 369:2001; pp. 351-355.

Ramachandran, et al., "Chemical Kinetics in Real Time: Using the Differential Rate Law and Discovering the Reaction Orders," A Physical Chemistry Laboratory Experiment, Journal of Chemical Education; 1996, pp. 686-689.

* cited by examiner

SYSTEMS, METHODS, AND APPARATUSES FOR IN SITU MONITORING OF CEMENT FLUID COMPOSITIONS AND SETTING PROCESSES THEREOF

BACKGROUND

The present invention relates to optical analysis systems, methods, and apparatuses for analyzing fluids and, in particular, to systems, methods, and apparatuses for monitoring fluids relating to cementing operations in or near real-time.

Cementing operations are often used in wellbores for, inter alia, supporting casings and liners, providing zonal isolation, and protecting the casing from corrosive formation fluids. In such operations, it is often important to precisely know the location, characteristics, and setting status of cement slurries as they are prepared, circulated into and through the wellbore, and set in the wellbore or other annulus therein. Even though a plurality of downhole tools are used in conjunction with the various steps of cementing operations, in situ analysis of cement fluid compositions during cementing operations is often not achievable with conventional monitoring systems, especially in conjunction with steps that encounter extreme environments such as in the wellbore. Accordingly, the location, characteristics, and setting status of cement slurries are often required to be extrapolated from laboratory data, calculations of volumes to be filled, and calculations based on the conditions in the wellbore (e.g., temperature).

Further, the integrity and/or efficacy of the downhole tools associated with the cementing operation are unknown unless a significant failure occurs. Accordingly, if a downhole tool has a minor malfunction, corrective action to mitigate any further problems cannot be taken. If the further problems impact the integrity of the resultant set cement, expensive and time consuming remedial operations may need to be undertaken.

As cementing operations are performed with a plurality of downhole tools and often performed multiple times during the lifetime of a well, in situ analysis of cement fluid compositions and analysis of downhole tool efficacy allow for proactive and/or responsive actions to be taken and, therefore, may be of value.

SUMMARY OF THE INVENTION

The present invention relates to optical analysis systems, methods, and apparatuses for analyzing fluids and, in particular, to systems, methods, and apparatuses for monitoring fluids relating to cementing operations in or near real-time.

One embodiment of the present invention includes a method that comprises containing a cement fluid composition in a flow path comprising a wellbore; and optically interacting the cement fluid composition with an integrated computational element, thereby generating an output signal corresponding to a characteristic of the cement fluid composition, the integrated computational element being coupled to a tool.

Another embodiment of the present invention includes a system that comprises a cementing plug arranged within a wellbore and in contact with one or more fluids; and at least one optical computing device arranged on the cementing plug for monitoring the one or more fluids, the at least one optical computing device having at least one integrated computational element configured to optically interact with the one or more fluids and thereby generate optically interacted light, and at least one detector arranged to receive the optically interacted light and generate an output signal corresponding to a characteristic of the one or more fluids.

Yet another embodiment of the present invention includes a system that comprises a flow path defined in a surface pack-off device and containing one or more fluids therein; and at least one optical computing device arranged in the flow path for monitoring the one or more fluids, the at least one optical computing device having at least one integrated computational element configured to optically interact with the one or more fluids and thereby generate optically interacted light, and at least one detector arranged to receive the optically interacted light and generate an output signal corresponding to a characteristic of the one or more fluids.

Another embodiment of the present invention includes a cementing method that comprises mixing a dry cement blend; measuring a characteristic of the dry cement blend by optically interacting the dry cement blend with a first integrated computational element, thereby generating a first output signal corresponding to the characteristic of the dry cement blend; adding water to the dry cement blend to yield a cement slurry; measuring a first characteristic of the cement slurry by optically interacting the cement slurry with a second integrated computational element, thereby generating a second output signal corresponding to the first characteristic of the cement slurry; introducing the cement slurry into a wellbore penetrating a subterranean formation; monitoring a location of the cement slurry in the wellbore by optically interacting the cement slurry with a first plurality of integrated computational elements located along the wellbore, thereby generating independently for each the first plurality of integrated computational elements a third output signal corresponding to a second characteristic of the cement slurry; allowing the cement slurry to set in the wellbore by a cement setting process; and monitoring a progress of the cement setting progress by optically interacting the cement slurry with a second plurality of integrated computational elements located along the wellbore, thereby generating independently for each the second plurality of integrated computational elements a fourth output signal corresponding to a characteristic of the cement setting progress.

The features and advantages of the present invention will be readily apparent to those skilled in the art upon a reading of the description of the preferred embodiments that follows.

BRIEF DESCRIPTION OF THE DRAWINGS

The following figures are included to illustrate certain aspects of the present invention, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
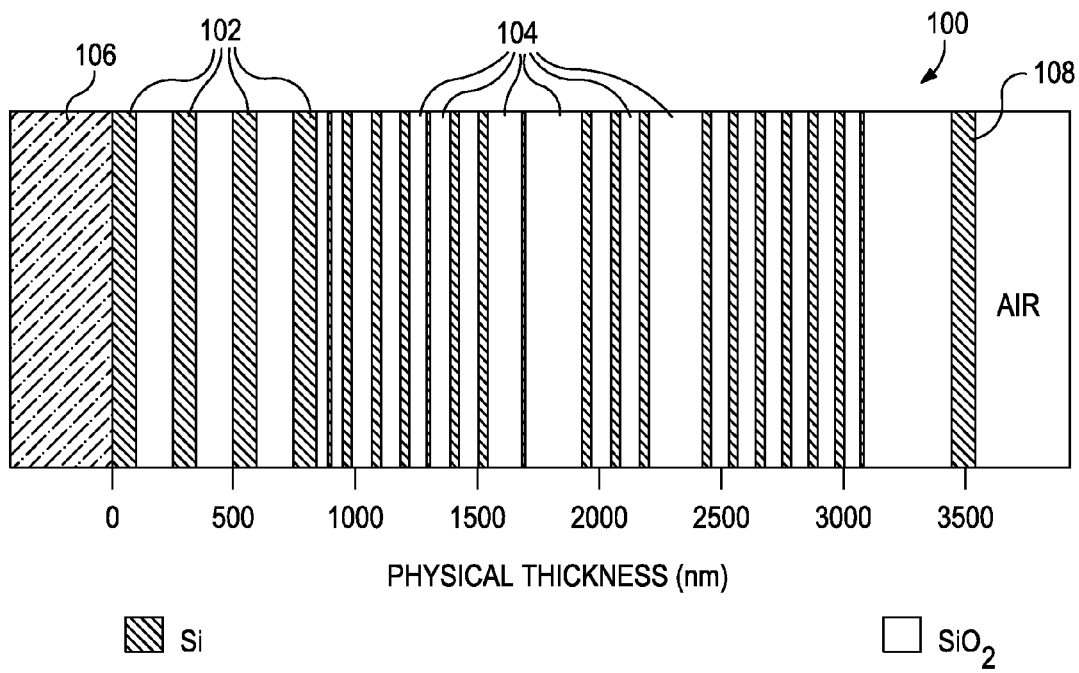
FIG. 1 illustrates an exemplary integrated computational element, according to one or more embodiments.

The present invention relates to optical analysis systems, methods, and apparatuses for analyzing fluids and, in particular, to systems, methods, and apparatuses for monitoring fluids relating to cementing operations in or near real-time.

The exemplary systems and methods described herein employ various configurations of optical computing devices, also commonly referred to as "opticoanalytical devices," for the real-time or near real-time monitoring of fluids useful in conjunction with cementing operations for determining and analyzing the properties, location, and/or history of a cement fluid composition. In operation, when used in conjunction with a downhole tool, the exemplary systems and methods may be useful and otherwise advantageous in several applications that may include, but are not limited to, monitoring the efficacy and/or integrity of the downhole tool.

The optical computing devices, which are described in more detail below, can advantageously provide real-time or near real-time monitoring of a cement fluid composition or other fluid relating thereto (e.g., a spacer fluid, a lost circulation treatment fluid, a displacement fluid, a flush fluid, and the like), including chemical reactions occurring within a cement fluid composition. In some instances, such monitoring cannot presently be achieved with either onsite analyses at a job site or via more detailed analyses that take place in a laboratory. A significant and distinct advantage of these devices is that they can be configured to specifically detect and/or measure a particular characteristic of interest of a fluid or other material in situ, thereby allowing qualitative and/or quantitative analyses to occur without having to extract a sample and undertake time-consuming analyses at an off-site laboratory. With the ability to undertake real-time or near real-time analyses, the exemplary systems and methods described herein may be able to provide some measure of proactive or responsive control over operational parameters, mitigate the need for other time-consuming operations performed as a result of a failure (minor or extreme) of a downhole tool, enable the collection and archival of information relating to cementing operations to optimize subsequent cementing operations, and/or enhance the capacity for remote job execution.

Those skilled in the art will readily appreciate that the systems and methods disclosed herein may be suitable for use in the oil and gas industry since the described optical computing devices provide a cost-effective, rugged, and accurate means for monitoring fluids and chemical reactions occurring therein in order to facilitate the efficient management of wellbore operations involving cement fluid compositions and cementing operations. It will be further appreciated, however, that the various disclosed systems and methods are equally applicable to other technology or industry fields including, but not limited to, the construction industry, industrial applications, mining industries, or any field where it may be advantageous to determine in real-time or near real-time the status of a cement setting process or other similar chemical reactions.

The optical computing devices suitable for use in the present embodiments can be deployed at any number of various points within a flow path to monitor a fluid, including, for determining and analyzing the properties, location, and/or history of a cement fluid composition. It should be noted that the location of a material of interest can be derived from detecting a characteristic of interest with an optical computing device having a known location (approximate or exact) or using two or more optical computing devices having known relative locations to each other.

Depending on the location of the particular optical computing device, various types of information about a cement fluid composition can be ascertained. In some cases, for example, the optical computing devices can be used to monitor a chemical reaction in real-time that relates to cement setting processes, for example, by determining the concentration of unreacted reagents and any resulting products relating to the cement setting process. This may prove advantageous in determining when the cement setting process has progressed to completion. Further, when such a characteristic of interest is measured over time (i.e., at or across a plurality of time points), the rate of the cement setting process may be derived. If the detected rate of the cement setting process is not optimal or otherwise as desired, corrective actions may then be taken. Thus, the systems and methods described herein may be configured to monitor a fluid and a chemical reaction process related thereto.

As used herein, the term "fluid" refers to any substance that is capable of flowing, including particulate solids, liquids, gases, slurries, emulsions, powders, muds, glasses, combinations thereof, and the like. In some embodiments, the fluid can be an aqueous fluid, including water or the like. In some embodiments, the fluid can be a non-aqueous fluid, including organic compounds, more specifically, hydrocarbons, oil, a refined component of oil, petrochemical products, and the like. In some embodiments, the fluid can be a treatment fluid, a spacer fluid, a cement fluid composition, a drilling fluid, or a formation fluid as found in the oil and gas industry. Fluids can include various flowable mixtures of solids, liquids, and/or gases. Illustrative gases that can be considered fluids according to the present embodiments include, for example, air, nitrogen, carbon dioxide, argon, hydrogen sulfide ($H_2S$), helium, methane, ethane, butane, and other hydrocarbon gases, combinations thereof and/or the like.

As used herein, the term "cement fluid composition" refers to any fluid that comprises a cement. Cement is not necessarily hydraulic cement, since other types of materials (e.g., polymers like epoxies and latexes) can be used in place of, or in addition to, a hydraulic cement. Examples of cements may include, but are not limited to, hydraulic cements, Portland cement, gypsum cements, calcium phosphate cements, high alumina content cements, silica cements, high alkalinity cements, shale cements, acid/base cements, magnesia cements (e.g., Sorel cements), fly ash cements, zeolite cement systems, cement kiln dust cement systems, slag cements, micro-fine cements, epoxies, bentonites, latexes, and the like, any derivative thereof, and any combination thereof. Cement fluid compositions may be cement slurries that include water or dry cement blends. Unless otherwise specified, the term "fluid" encompasses cement fluid compositions, the term "cement fluid compositions" encompasses cement slurries and dry cement blends, and the term "cement slurry" encompasses foamed cements. As used herein, the term "dry cement blend" refers to a mixture of solid particles including at least some cement particles and is not hydrated beyond about ambient conditions (e.g., no additional water has been added).

As used herein, the term "chemical reaction process" or "chemical reaction" refers to a process that leads to the transformation of one set of chemical substances to another. As known to those skilled in the art, chemical reactions involve one or more reagents, as described below, that chemically react either spontaneously, requiring no input of energy, or non-spontaneously typically following the input of some type of energy, such as heat, light, or electricity. The chemical reaction process yields one or more products, which may or may not have properties different from the reagents.

As used herein, the term "cement setting process" refers to the chemical reaction(s) that cause a cement slurry to harden into a cement. Chemical reactions of cement setting processes described herein may include, but are not limited to, hydration reactions (e.g., reactions between hydraulic cements and water), crosslinking reactions (e.g., polymer crosslinking reactions and reactions between 2-component epoxies), and the like, and any combination thereof. As used herein, the term "hydraulic cement" refers to a cement that hardens in the presence of water. Changes in characteristics that may be useful in providing the status of a cement setting process may include, but are not limited to, an increase in particle size, a plateau of an exothermic reaction, a decrease in the concentration of a reagent (e.g., water), an increase in the concentration of a product (e.g., a base like calcium hydroxide), and the like, and any combination thereof. Unless otherwise specified, the term "chemical reaction process" encompasses a cement setting process.

As used herein, the term "cementing operation" encompasses any subterranean operation utilizing a cement fluid composition, e.g., primary cementing operations, secondary cementing operations, squeeze operations, remedial cementing operations, casing operations, plugging operations, and the like including any with traditional or reverse fluid flow directions.

As used herein, the term "characteristic" refers to a chemical, mechanical, or physical property (quantitative or qualitative) of a material of interest (e.g., a set cement, a spacer fluid, a cement fluid composition, a lost circulation treatment fluid, and the like) or analyte thereof. As used herein, the term "analyte" refers to a chemical component of the material of interest. The term analyte encompasses both chemical components involved in a chemical reaction (e.g., reagents and products) and chemical components not involved in a chemical reaction transpiring within the material of interest. Illustrative characteristics of a material of interest that can be monitored with the optical computing devices disclosed herein can include, for example, chemical composition (e.g., identity and concentration in total or of individual analytes), impurity content, pH, viscosity, density, ionic strength, total dissolved solids, salt content, porosity, opacity, bacteria content, particle size distribution, color, temperature, hydration level, oxidation state, and the like. Moreover, the phrase "characteristic of interest" may be used herein to refer to a characteristic of a material of interest, which encompasses a characteristic of an analyte thereof and a characteristic of a chemical reaction transpiring or otherwise occurring therein. It should be noted that as used herein, the term "material of interest" encompasses analytes of such a material. Accordingly, embodiments described herein relative to a material of interest encompass similar embodiments that are relative to an analyte or analytes of the material of interest.

Exemplary analytes may include, but are not limited to, water, salts, minerals (wollastonite, metakaolin, and pumice), cements (Portland cement, gypsum cements, calcium phosphate cements, high alumina content cements, silica cements, and high alkalinity cements), fillers (e.g., fly ash, fume silica, hydrated lime, pozzolanic materials, sand, barite, calcium carbonate, ground marble, iron oxide, manganese oxide, glass bead, crushed glass, crushed drill cutting, ground vehicle tire, crushed rock, ground asphalt, crushed concrete, crushed cement, ilmenite, hematite, silica flour, fume silica, fly ash, elastomers, polymers, diatomaceous earth, a highly swellable clay mineral, nitrogen, air, fibers, natural rubber, acrylate butadiene rubber, polyacrylate rubber, isoprene rubber, chloroprene rubber, butyl rubber, brominated butyl rubber, chlorinated butyl rubber, chlorinated polyethylene, neoprene rubber, styrene butadiene copolymer rubber, sulphonated polyethylene, ethylene acrylate rubber, epichlorohydrin ethylene oxide copolymer, ethylene propylene rubber, ethylene propylene diene terpolymer rubber, ethylene vinyl acetate copolymer, fluorosilicone rubber, silicone rubber, poly-2,2,1-bicycloheptene (polynorbomeane), alkylstyrene, crosslinked substituted vinyl acrylate copolymer, nitrile rubber (butadiene acrylonitrile copolymer), hydrogenated nitrile rubber, fluoro rubber, perfluoro rubber, tetraflouroethylene/propylene, starch polyacrylate acid graft copolymer, polyvinyl alcohol cyclic acid anhydride graft copolymer, isobutylene maleic anhydride, acrylic acid type polymer, vinylacetate-acrylate copolymer, polyethylene oxide polymer, carboxymethyl cellulose polymer, starch-polyacrylonitrile graft copolymer, polymethacrylate, polyacrylamide, and non-soluble acrylic polymer), hydrocarbons, acids, acid-generating compounds, bases, base-generating compounds, biocides, surfactants, scale inhibitors, corrosion inhibitors, gelling agents, crosslinking agents, anti-sludging agents, foaming agents, defoaming agents, antifoam agents, emulsifying agents, de-emulsifying agents, iron control agents, proppants or other particulates, gravel, particulate diverters, salts, cement slurry loss control additives, gas migration control additives, gases, air, nitrogen, carbon dioxide, hydrogen sulfide ($H_2S$), argon, helium, hydrocarbon gases, methane, ethane, butane, catalysts, clay control agents, chelating agents, corrosion inhibitors, dispersants, flocculants, scavengers (e.g., $H_2S$ scavengers, $CO_2$ scavengers, or $O_2$ scavengers), lubricants, breakers, delayed release breakers, friction reducers, bridging agents, viscosifiers, weighting agents, solubilizers, rheology control agents, viscosity modifiers, pH control agents (e.g., buffers), hydrate inhibitors, relative permeability modifiers, diverting agents, consolidating agents, fibrous materials, bactericides, tracers, probes, nanoparticles, paraffin waxes, asphaltenes, foams, sand or other solid particles, and the like. Combinations of these components can be used as well.

As used herein, the term "flow path" refers to a route through which a fluid is capable of being transported between two points. In some cases, the flow path need not be continuous or otherwise contiguous between the two points. Exemplary flow paths include, but are not limited to, a slurry tank, a flowline, a pipeline, a conduit, a wellbore annulus (e.g., an annulus between a casing and a wellbore or an annulus between a screen and a wellbore), a casing, a liner, a liner string, a hose, a mixer, a pump, a process facility, a storage vessel, a tanker, a railway tank car, a transport barge or ship, a separator, a contactor, a process vessel, and the like, any hybrid thereof, and any combination thereof. In cases where the flow path is a pipeline, or the like, the pipeline may be a pre-commissioned pipeline or an operational pipeline. It should be noted that the term "flow path" does not necessarily imply that a fluid is flowing therein, rather that a fluid is capable of being transported or otherwise flowable therethrough. In some embodiments, a flow path may be a component of a more complex system, for example, skids, trucks, pumps, and the like. In some embodiments, a flow path may comprise more than one section that is separated, but still fluidly communicable, by apparatuses like valves, flow meters, and the like.

As used herein, the term "electromagnetic radiation" refers to radio waves, microwave radiation, infrared and near-infrared radiation, visible light, ultraviolet light, X-ray radiation, and gamma ray radiation.

As used herein, the term "optical computing device" refers to an optical device that is configured to receive an input of electromagnetic radiation from a material of interest and produce an output of electromagnetic radiation from a processing element arranged within the optical computing device. The processing element may be, for example, an integrated computational element (ICE) used in the optical computing device. As discussed in greater detail below, the electromagnetic radiation that optically interacts with the processing element is changed so as to be readable by a detector, such that an output of the detector can be correlated to at least one characteristic of the material of interest, such as a characteristic of a chemical process of interest transpiring in the material of interest. The output of electromagnetic radiation from the processing element can be reflected electromagnetic radiation, transmitted electromagnetic radiation, and/or dispersed electromagnetic radiation. Whether reflected, transmitted, or dispersed, electromagnetic radiation is eventually analyzed by the detector and may be dictated by the structural parameters of the optical computing device as well as other considerations known to those skilled in the art. In addition, emission and/or scattering of the substance, for example via fluorescence, luminescence, Raman scattering, and/or Raleigh scattering, can also be monitored by the optical computing devices.

As used herein, the term "optically interact" or variations thereof refers to the reflection, transmission, scattering, diffraction, or absorption of electromagnetic radiation either on, through, or from one or more processing elements (i.e., integrated computational elements). Accordingly, optically interacted light refers to light that has been reflected, transmitted, scattered, diffracted, or absorbed by, emitted, or re-radiated, for example, using the integrated computational elements, but may also apply to interaction with a material of interest.

The exemplary systems and methods described herein will include at least one optical computing device arranged along or in a flow path in order to monitor a characteristic of a material of interest (flowing or otherwise contained within the flow path) and calculate changes in the characteristic of interest. The exemplary systems and methods described herein may, in some embodiments, include at least two optical computing devices strategically arranged along a flow path in order to monitor a characteristic of a material of interest flowing or otherwise contained therein and calculate differences between the characteristic of interest at the various measurements or monitoring locations. An optical computing device may include an electromagnetic radiation source, at least one processing element (e.g., integrated computational elements), and at least one detector arranged to receive optically interacted light from the at least one processing element. As disclosed below, however, in at least one embodiment, the electromagnetic radiation source may be omitted and instead the electromagnetic radiation may be derived from the material of interest itself. For example, in some embodiments, a tracer may be incorporated into a cement fluid and/or dry cement blend that is a dye with a strong chromophore or charge-transfer group that would allow for the electromagnetic radiation to be derived from an analyte (i.e., the tracer) in the cement fluid and/or dry cement blend. In some embodiments, the exemplary optical computing devices may be specifically configured for detecting, analyzing, and quantitatively measuring a particular characteristic of the material of interest in the flow path. In other embodiments, the optical computing devices may be general purpose optical devices, with post-acquisition processing (e.g., through computer means) being used to specifically detect the characteristic of interest.

In some embodiments, suitable structural components for the exemplary optical computing devices are described in commonly owned U.S. Pat. No. 6,198,531 entitled "Optical Computational System;" U.S. Pat. No. 6,529,276 entitled "Optical Computational System;" U.S. Pat. No. 7,123,844 entitled "Optical Computational System;" U.S. Pat. No. 7,834,999 entitled "Optical Analysis System and Optical Train;" U.S. Pat. No. 7,911,605 entitled "Multivariate Optical Elements for Optical Analysis System;" U.S. Pat. No. 7,920,258 entitled "Optical Analysis System and Elements to Isolate Spectral Region;" and U.S. Pat. No. 8,049,881 entitled "Optical Analysis System and Methods for Operating Multivariate Optical Elements in a Normal Incidence Orientation;" each of which is incorporated herein by reference in its entirety, and U.S. patent application Ser. No. 12/094,460 entitled "Methods of High-Speed Monitoring Based on the Use of Multivariate Optical Elements;" Ser. No. 12/094,465 entitled "Optical Analysis System for Dynamic Real-Time Detection and Measurement;" and Ser. No. 13/456,467 entitled "Imaging Systems for Optical Computing Devices;" each of which is also incorporated herein by reference in its entirety. As will be appreciated, variations of the structural components of the optical computing devices described in the above-referenced patents and patent applications may be suitable, without departing from the scope of the disclosure, and therefore, should not be considered limiting to the various embodiments or uses disclosed herein.

The optical computing devices described in the foregoing patents and patent applications combine the advantage of the power, precision and accuracy associated with laboratory spectrometers, while being extremely rugged and suitable for field use. Furthermore, the optical computing devices can perform calculations (analyses) in real-time or near real-time without the need for time-consuming sample processing. In this regard, the optical computing devices can be specifically configured to detect and analyze particular characteristics of interest (e.g., hydration levels, the concentration of analytes, temperature, and the like as described herein). As a result, interfering signals are discriminated from those of interest in the material of interest by appropriate configuration of the optical computing devices, such that the optical computing devices provide a rapid response regarding the characteristics of interest as based on the detected output. In some embodiments, the detected output can be converted into a voltage that is distinctive of the magnitude of the characteristic of interest being measured. The foregoing advantages and others make the optical computing devices particularly well suited for field and downhole use, but may equally be applied to several other technologies or industries, without departing from the scope of the disclosure.

The optical computing devices can be configured to detect not only the composition and concentrations of an analyte in a material of interest (e.g. a fluid or a solid like a set cement), but they also can be configured to determine physical properties and other characteristics of the material of interest as well, based on their analysis of the electromagnetic radiation received from the particular material of interest. For example, the optical computing devices can be configured to determine a characteristic of interest, e.g., a concentration of a reagent or product, and correlate the determined characteristic to the status of a cement setting process by using suitable processing means. As will be appreciated, the optical computing devices may be configured to detect as many characteristics of interest as desired. All that is required to accomplish the monitoring of multiple characteristics is the incorporation of suitable processing and detection means within the optical computing device for each characteristic of interest, whether pertaining to the material of interest or an analyte thereof. In some embodiments, the cement setting status can be determined using a combination of characteristics of interest (e.g., a linear, non-linear, logarithmic, and/or exponential combinations). Accordingly, the more characteristics of interest that are detected and analyzed using the optical computing devices, the more accurately the cement setting status and/or fluid composition can be determined.

The optical computing devices described herein utilize electromagnetic radiation to perform calculations, as opposed to the hardwired circuits of conventional electronic processors. When electromagnetic radiation interacts with a material of interest, unique physical and chemical information about the material of interest may be encoded in the electromagnetic radiation that is reflected from, transmitted through, or radiated therefrom. This information is often referred to as the spectral "fingerprint" of the material of interest. The optical computing devices described herein are capable of extracting the information of the spectral fingerprint of multiple characteristics of a material of interest (e.g., a fluid or a solid like a set cement including an analyte thereof), and converting that information into a detectable output regarding the overall properties of the monitored material of interest. That is, through suitable configurations of the optical computing devices, electromagnetic radiation associated with characteristics of a material of interest can be separated from electromagnetic radiation associated with all other components of the material of interest in order to estimate the properties of the monitored substance in real-time or near real-time.

The processing elements used in the exemplary optical computing devices described herein may be characterized as integrated computational elements (ICE). Each ICE is capable of distinguishing electromagnetic radiation related to the characteristic of interest from electromagnetic radiation related to other components of a material of interest. Referring to FIG. 1, illustrated is an exemplary ICE 100 suitable for use in the optical computing devices used in the systems and methods described herein. As illustrated, the ICE 100 may include a plurality of alternating layers 102 and 104, such as silicon (Si) and $SiO_2$ (quartz), respectively. In general, these layers 102, 104 consist of materials whose index of refraction is high and low, respectively. Other examples might include niobia and niobium, germanium and germania, MgF, $SiO_x$, and other high and low index materials known in the art. The layers 102, 104 may be strategically deposited on an optical substrate 106. In some embodiments, the optical substrate 106 is BK-7 optical glass. In other embodiments, the optical substrate 106 may be another type of optical substrate, such as quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite the optical substrate 106 in FIG. 1), the ICE 100 may include a layer 108 that is generally exposed to the environment of the device or installation. The number of layers 102, 104 and the thickness of each layer 102, 104 are determined from the spectral attributes acquired from a spectroscopic analysis of a characteristic of interest using a conventional spectroscopic instrument. The spectrum of interest of a given characteristic of interest typically includes any number of different wavelengths. It should be understood that the exemplary ICE 100 in FIG. 1 does not in fact represent any particular characteristic of interest, but is provided for purposes of illustration only. Consequently, the number of layers 102, 104 and their relative thicknesses, as shown in FIG. 1, bear no correlation to any particular characteristic of interest. Nor are the layers 102, 104 and their relative thicknesses necessarily drawn to scale, and therefore should not be considered limiting of the present disclosure. Moreover, those skilled in the art will readily recognize that the materials that make up each layer 102, 104 (i.e., Si and $SiO_2$) may vary, depending on the application, cost of materials, and/or applicability of the materials to the monitored substance.

In some embodiments, the material of each layer 102, 104 can be doped or two or more materials can be combined in a manner to achieve the desired optical characteristic. In addition to solids, the exemplary ICE 100 may also contain liquids and/or gases, optionally in combination with solids, in order to produce a desired optical characteristic. In the case of gases and liquids, the ICE 100 can contain a corresponding vessel (not shown), which houses the gases or liquids. Exemplary variations of the ICE 100 may also include holographic optical elements, gratings, piezoelectric, light pipe, digital light pipe (DLP), variable optical attenuators, and/or acousto-optic elements, for example, that can create transmission, reflection, and/or absorptive properties of interest.

The multiple layers 102, 104 exhibit different refractive indices. By properly selecting the materials of the layers 102, 104 and their relative thickness and spacing, the ICE 100 may be configured to selectively pass/reflect/refract predetermined fractions of electromagnetic radiation at different wavelengths. Each wavelength is given a predetermined weighting or loading factor. The thickness and spacing of the layers 102, 104 may be determined using a variety of approximation methods from the spectrograph of the characteristic of interest. These methods may include inverse Fourier transform (IFT) of the optical transmission spectrum and structuring the ICE 100 as the physical representation of the IFT. The approximations convert the IFT into a structure based on known materials with constant refractive indices. Further information regarding the structures and design of exemplary integrated computational elements (also referred to as multivariate optical elements) is provided in Applied Optics, Vol. 35, pp. 5484-5492 (1996) and Vol. 129, pp. 2876-2893, which is hereby incorporated by reference.

The weightings that the layers 102, 104 of the ICE 100 apply at each wavelength are set to the regression weightings described with respect to a known equation, or data, or spectral signature. Briefly, the ICE 100 may be configured to perform the dot product of the input light beam into the ICE 100 and a desired loaded regression vector represented by each layer 102, 104 for each wavelength. As a result, the output light intensity of the ICE 100 is related to the characteristic of interest. Further details regarding how the exemplary ICE 100 is able to distinguish and process electromagnetic radiation related to the characteristic of interest are described in U.S. Pat. No. 6,198,531 entitled "Optical Computational System;" U.S. Pat. No. 6,529,276 entitled "Optical Computational System;" and U.S. Pat. No. 7,920,258 entitled "Optical Analysis System and Elements to Isolate Spectral Region;" previously incorporated herein by reference.

Figure 2:
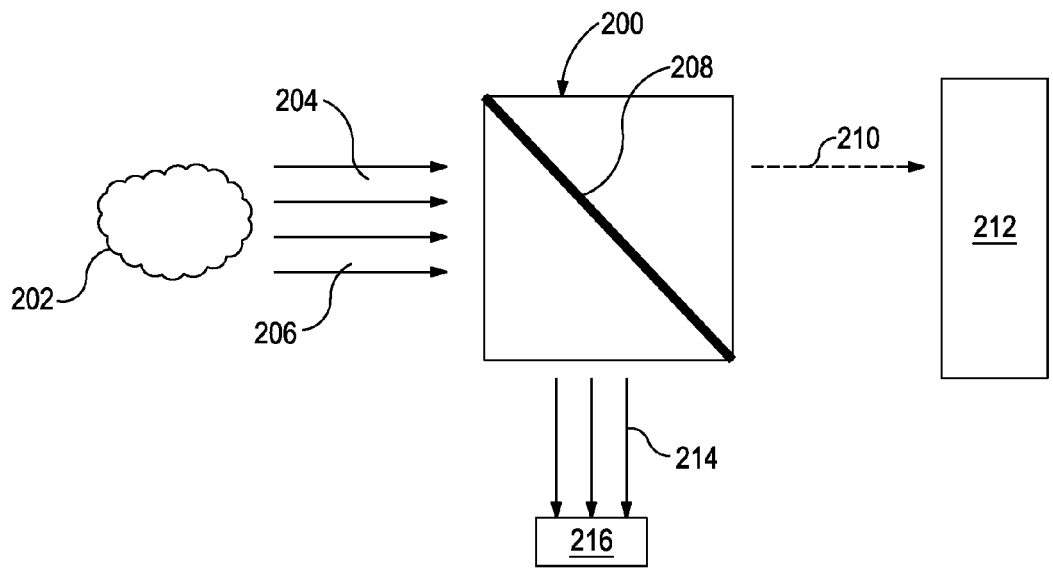
FIG. 2 illustrates a block diagram non-mechanistically illustrating how an optical computing device distinguishes electromagnetic radiation related to a characteristic of interest from other electromagnetic radiation, according to one or more embodiments.

Referring now to FIG. 2, illustrated is a block diagram that non-mechanistically illustrates how an optical computing device 200 is able to distinguish electromagnetic radiation related to a characteristic of interest from other electromagnetic radiation. As shown in FIG. 2, after being illuminated with incident electromagnetic radiation, a material of interest 202 having a characteristic of interest produces an output of electromagnetic radiation (e.g., sample-interacted light), some of which is electromagnetic radiation 204 corresponding to the characteristic of interest and some of which is background electromagnetic radiation 210 corresponding to other components or characteristics of the material of interest 202. In some embodiments, the material of interest 202 may include one or more characteristics of interest that may correspond to the one or more analytes of the material of interest (e.g., reagents, products, or other chemical components).

Although not specifically shown, one or more spectral elements may be employed in the device 200 in order to restrict the optical wavelengths and/or bandwidths of the system and thereby eliminate unwanted electromagnetic radiation existing in wavelength regions that have no importance. Such spectral elements can be located anywhere along the optical train, but are typically employed directly after a light source, which provides the initial electromagnetic radiation. Various configurations and applications of spectral elements in optical computing devices may be found in commonly owned U.S. Pat. No. 6,198,531 entitled "Optical Computational System;" U.S. Pat. No. 6,529,276 entitled "Optical Computational System;" U.S. Pat. No. 7,123,844 entitled "Optical Computational System;" U.S. Pat. No. 7,834,999 "Optical Analysis System and Optical Train;" U.S. Pat. No. 7,911,605 entitled "Multivariate Optical Elements for Optical Analysis System;" U.S. Pat. No. 7,920,258 entitled "Optical Analysis System and Elements to Isolate Spectral Region;" and U.S. Pat. No. 8,049,881 entitled "Optical Analysis System and Methods for Operating Multivariate Optical Elements in a Normal Incidence Orientation;" and U.S. patent application Ser. No. 12/094,460 entitled "Methods of High-Speed Monitoring Based on the Use of Multivariate Optical Elements;" Ser. No. 12/094,465 entitled "Optical Analysis System for Dynamic Real-Time Detection and Measurement;" and Ser. No. 13/456,467 entitled "Imaging Systems for Optical Computing Devices;" incorporated herein by reference, as indicated above.

The beams of electromagnetic radiation 204, 206 impinge upon the optical computing device 200, which contains an exemplary ICE 208 therein. In the illustrated embodiment, the ICE 208 may be configured to produce optically interacted light, for example, transmitted optically interacted light 210 and reflected optically interacted light 214. In operation, the ICE 208 may be configured to distinguish the electromagnetic radiation 204 from the background electromagnetic radiation 206.

The transmitted optically interacted light 210, which may be related to a characteristic of interest in the material of interest 202, may be conveyed to a detector 212 for analysis and quantification. In some embodiments, the detector 212 is configured to produce an output signal in the form of a voltage that corresponds to the particular characteristic of interest of the material of interest 202. In at least one embodiment, the signal produced by the detector 212 and the concentration of the characteristic of interest may be directly proportional. In other embodiments, the relationship may be a polynomial function, an exponential function, and/or a logarithmic function. The reflected optically interacted light 214, which may be related to characteristics of other components of the material of interest 202, can be directed away from detector 212. In alternative configurations, the ICE 208 may be configured such that the reflected optically interacted light 214 can be related to the characteristic of interest, and the transmitted optically interacted light 210 can be related to other components or characteristics of the material of interest 202.

In some embodiments, a second detector 216 can be present and arranged to detect the reflected optically interacted light 214. In other embodiments, the second detector 216 may be arranged to detect the electromagnetic radiation 204, 206 derived from the material of interest 202 or electromagnetic radiation directed toward or before the material of interest 202. Without limitation, the second detector 216 may be used to detect radiating deviations stemming from an electromagnetic radiation source (not shown), which provides the electromagnetic radiation (i.e., light) to the device 200. For example, radiating deviations can include such things as, but not limited to, intensity fluctuations in the electromagnetic radiation, interferent fluctuations (e.g., dust or other interferents passing in front of the electromagnetic radiation source), coatings on windows included with the optical computing device 200, combinations thereof, or the like. In some embodiments, a beam splitter (not shown) can be employed to split the electromagnetic radiation 204, 206, and the transmitted or reflected electromagnetic radiation can then be directed to two or more ICE 208. That is, in such embodiments, the ICE 208 does not function as a type of beam splitter, as depicted in FIG. 2, and the transmitted or reflected electromagnetic radiation simply passes through the ICE 208, being computationally processed therein, before travelling to the detector 212.

The characteristic(s) of interest being analyzed using the optical computing device 200 can be further processed and/or analyzed computationally to provide additional characterization information about the material of interest 202. In some embodiments, the identification and concentration of each analyte of interest in the material of interest 202 can be used to predict certain physical properties of the material of interest 202. For example, the bulk properties of the material of interest 202 can be estimated by using a combination of the properties conferred to the material of interest 202 by each analyte.

In some embodiments, the concentration or magnitude of the characteristic of interest determined using the optical computing device 200 can be fed into an algorithm operating under computer control. The algorithm may be configured to make predictions on how the properties of the material of interest 202 would change if the concentrations of the characteristic of interest are changed relative to one another. In some embodiments, the algorithm can produce an output that is readable by an operator who can manually take appropriate action, if needed, based upon the reported output. In other embodiments, however, the algorithm can take proactive process control by, for example, automatically adjusting the flow rate of a fluid through a flow path, introducing an analyte to a fluid to change a reaction rate, adjusting the temperature of a fluid to change a reaction rate, adjusting the density of the fluid, and the like.

In some embodiments, the characteristics of interest determined using the optical computing devices 200 can be associated with a timestamp. A timestamp may be useful in reviewing and analyzing the history of the characteristic of interest, which may be of added value in building a library of cement setting processes. In some embodiments, the characteristics of interest, optionally timestamped, can be fed into an algorithm operating under computer control. The algorithm may be configured to make predictions on the status of the cement setting process and/or any operational parameters that need to be changed as described herein. In some embodiments, the algorithm can produce an output that is readable by an operator who can manually take appropriate action, like initiation of a remedial operation, if needed, based upon the output.

The algorithm can be part of an artificial neural network configured to use the magnitude or concentration of each characteristic of interest in order to evaluate the overall property(s) of the material of interest 202 and predict how to modify the material of interest 202 in order to alter its properties in a desired way. Illustrative but non-limiting artificial neural networks are described in commonly owned U.S. patent application Ser. No. 11/986,763 entitled "Determining Stimulation Design Parameters Using Artificial Neural Networks Optimized with a Genetic Algorithm," which is incorporated herein by reference. It is to be recognized that an artificial neural network can be trained using samples of predetermined characteristics of interest, such as known reagents and products resulting from chemical processes involving such reagents, having known concentrations, compositions, and/or properties, and thereby generating a virtual library. As the virtual library available to the artificial neural network becomes larger, the neural network can become more capable of accurately predicting the characteristic of interest corresponding to the material of interest (including specific analytes thereof). Furthermore, with sufficient training, the artificial neural network can more accurately predict the properties of the material of interest, even in the presence of unknown analytes.

It is recognized that the various embodiments herein directed to computer control and artificial neural networks, including various blocks, modules, elements, components, methods, and algorithms, can be implemented using computer hardware, software, combinations thereof, and the like. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable read only memory (EPROM)), registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

In some embodiments, the data collected using the optical computing devices can be archived along with data associated with operational parameters being logged at a job site. Evaluation of job performance can then be assessed and improved for future operations or such information can be used to design subsequent operations. In addition, the data and information can be communicated (wired or wirelessly) to a remote location by a communication system (e.g., satellite communication or wide area network communication) for further analysis. The communication system can also allow remote monitoring and operation of a chemical reaction process to take place. Automated control with a long-range communication system can further facilitate the performance of remote job operations. In particular, an artificial neural network can be used in some embodiments to facilitate the performance of remote job operations. That is, remote job operations can be conducted automatically in some embodiments. In other embodiments, however, remote job operations can occur under direct operator control, where the operator is not at the job site (e.g., via wireless technology).

Figure 3A:
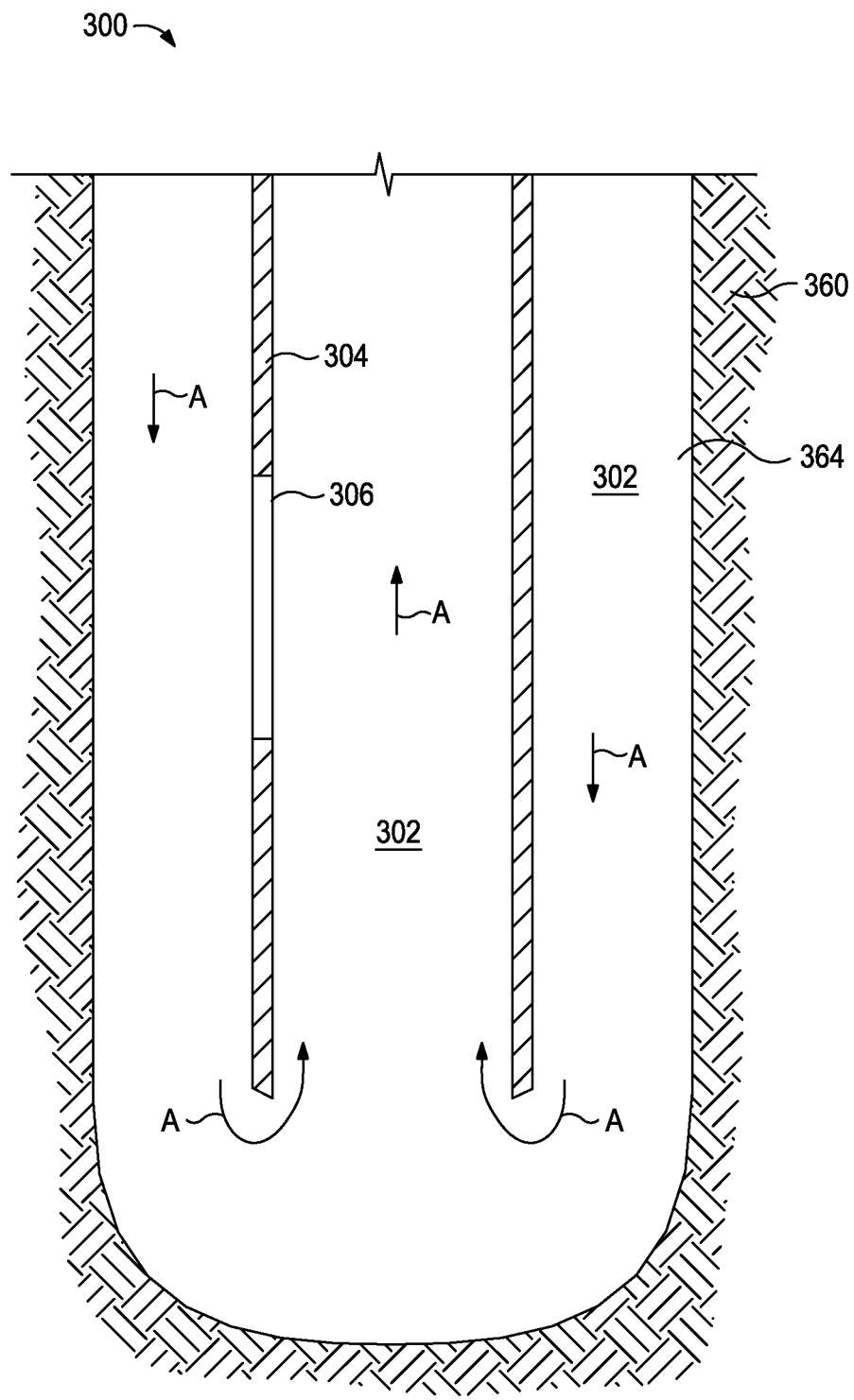
FIGS. 3A-B illustrate an exemplary system for monitoring a material of interest, according to one or more embodiments.

Referring now to FIG. 3A, illustrated is an exemplary system 300 for monitoring a fluid, such as a chemical reaction process that may occur within the fluid and/or to ascertain the location of the fluid, according to one or more embodiments. In the illustrated embodiment, the fluid may be contained or otherwise flowing within an exemplary flow path shown as an annulus 364 defined between a wellbore 360 and a casing 304. In at least one embodiment, the fluid present therein may be flowing in the general direction indicated by the arrows A (e.g., in a reverse cementing operation). As will be appreciated, however, in other embodiments the flow path may be any other type of flow path, as generally described or otherwise defined herein. For example, the flow path may be a storage or reaction vessel and the fluid may not necessarily be flowing while being monitored.

With continued reference to FIG. 3A, the system 300 may include at least one optical computing device 306, which may be similar in some respects to the optical computing device 200 of FIG. 2, and therefore may be best understood with reference thereto. The optical computing device 306 may be housed within a casing or housing (not shown) configured to substantially protect the internal components of the optical computing device 306 from damage or contamination from the external environment. The housing may operate to mechanically couple the optical computing device 306 to the casing 304 with, for example, mechanical fasteners, brazing or welding techniques, adhesives, magnets, combinations thereof and the like. In operation, the housing may be designed to withstand the pressures that may be experienced within or outside the flow path and thereby provide a fluid tight seal against external contamination.

As described in greater detail below, the optical computing device 306 may be useful in determining a particular characteristic of interest of the fluid within the flow path, e.g., determining a concentration of an analyte (e.g., reagent or product) present within the fluid. Knowing the presence and/or concentration of analytes found in the fluid may help determine, in some embodiments, (1) the location of a cement fluid composition (e.g., by correlating the presence of an analyte associated with the fluid to the location of the optical computing device 306) and/or (2) the status of the cement setting processes of the cement slurry.

In some embodiments, the location of a cement fluid composition may be determined relative to a spacer fluid before or after the cement fluid. That is, in some embodiments, an analyte of a spacer fluid may be analyzed with the optical computing device 306 to determine the location of a cement fluid composition. In other embodiments, the characteristic of interest may be a characteristic that two or more fluids have, but at different magnitudes so as to indicate which fluid is currently present. For example, particle size distribution may be relevant to both a spacer fluid and a cement fluid composition with the spacer fluid having a smaller particle size distribution and the cement fluid composition having a higher particle size distribution, and the optical computing device 306 may be configured to monitor and detect each.

Knowing any one of the foregoing may provide guidance to an operator as to parameters of the current operation or subsequent operations. For example, knowing the precise location of the cement fluid composition within a flow path may be useful in determining appropriate pumping speeds of the cement fluid composition. In other instances, knowing the precise location of the cement fluid composition as opposed to a calculated location (i.e., the location of the cement fluid composition calculated using, inter alia, the amount of cement fluid composition introduced, the flow rate, and the estimated volume to be filled) may be used to determine if the amount of cement fluid composition used in a particular cementing operation should be changed so as to prevent an unnecessary second cementing operation if too little is used. An accurate determination of the location of the cement fluid composition within the flow path may also forego the need for remedial operations (e.g., drill-out operations) in the event too much cement fluid composition is used and sets within, for example, a wellbore. In yet other instances, comparing the location of the cement fluid composition to its calculated location may be useful in determining if damage has occurred to the flow path, for example, where cement may be leaking from a wellbore into, and perhaps damaging, the adjacent subterranean formation.

The optical computing device 306 is illustrated in FIG. 3A as an integral part of the casing 304. One skilled in the art would understand that the optical computing device 306 may be coupled to the casing 304 so as to be disposed on a surface of the casing 304, partially integrated into a wall of the casing 304, extend outwardly beyond a surface of the casing 304, be flush with a surface of the casing 304, and any hybrid thereof. In some embodiments, the optical computing device 306 may be coupled to the casing 304 so as to monitor a fluid in the annulus 364 and/or the casing 304.

Figure 3B:
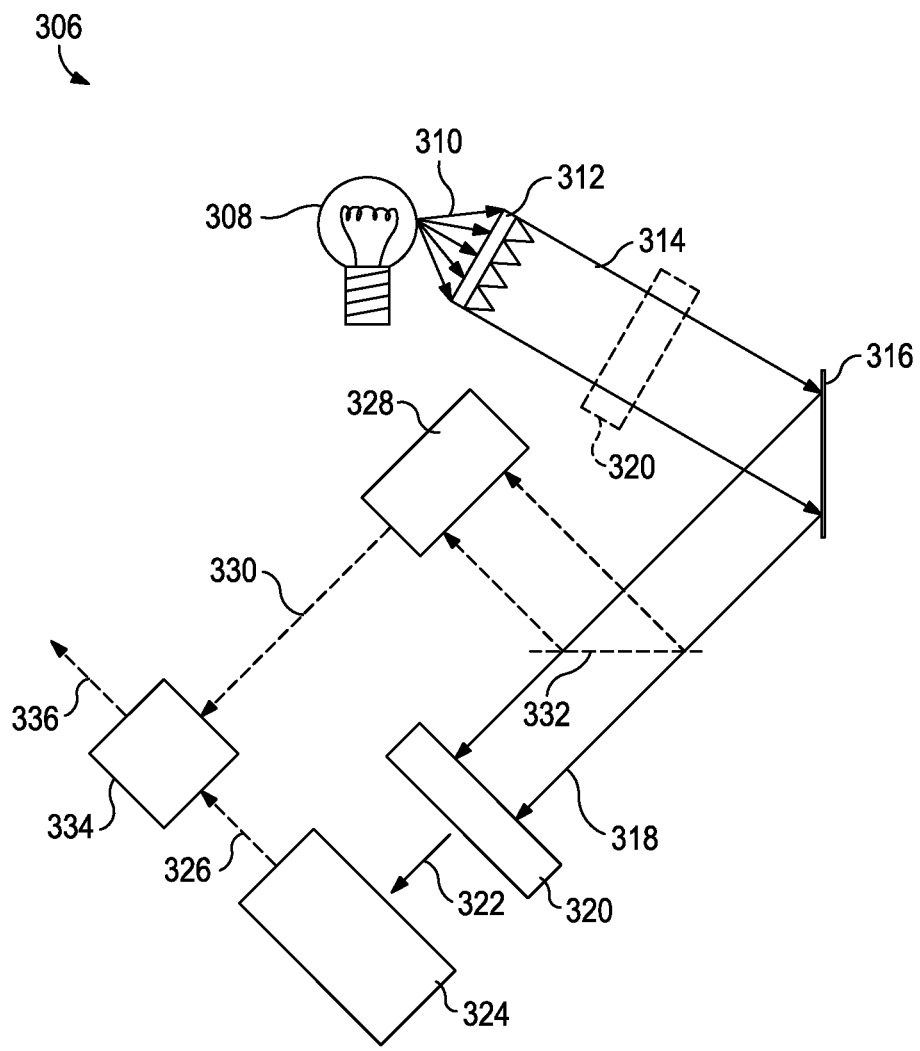

Referring now to FIG. 3B, with continued reference to FIG. 3A, the optical computing device 306 may include an electromagnetic radiation source 308 configured to emit or otherwise generate electromagnetic radiation 310. The electromagnetic radiation source 308 may be any device capable of emitting or generating electromagnetic radiation, as defined herein. For example, the electromagnetic radiation source 308 may be a light bulb, a light emitting device (LED), a laser, a blackbody, a photonic crystal, an X-Ray source, combinations thereof, or the like. In some embodiments, a lens 312 may be configured to collect or otherwise receive the electromagnetic radiation 310 and direct a beam 314 of electromagnetic radiation 310 toward a fluid 302 (e.g., a cement fluid composition). The lens 312 may be any type of optical device configured to transmit or otherwise convey the electromagnetic radiation 310 as desired. For example, the lens 312 may be a normal lens, a Fresnel lens, a diffractive optical element, a holographic graphical element, a mirror (e.g., a focusing mirror), a type of collimator, or any other electromagnetic radiation transmitting device known to those skilled in art. In other embodiments, the lens 312 may be omitted from the optical computing device 306 and the electromagnetic radiation 310 may instead be conveyed toward the fluid 302 directly from the electromagnetic radiation source 308.

In one or more embodiments, the optical computing device 306 may also include a sampling window 316 arranged adjacent to or otherwise in contact with the fluid 302 (e.g., the fluid contained in the flow paths described above in FIG. 3A) for detection purposes. The sampling window 316 may be made from a variety of transparent, rigid or semi-rigid materials that are configured to allow transmission of the electromagnetic radiation 310 therethrough. For example, the sampling window 316 may be made of, but is not limited to, glasses, plastics, semi-conductors, crystalline materials, polycrystalline materials, hot or cold-pressed powders, combinations thereof, or the like. In order to remove ghosting or other imaging issues resulting from reflectance on the sampling window 316, the system 300 may employ one or more internal reflectance elements (IRE), such as those described in co-owned U.S. Pat. No. 7,697,141 entitled "In Situ Optical Computational Fluid Analysis System and Method," and/or one or more imaging systems, such as those described in co-owned U.S. patent application Ser. No. 13/456,467 entitled "Imaging Systems for Optical Computing Devices," the contents of each hereby being incorporated by reference.

After passing through the sampling window 316, the electromagnetic radiation 310 impinges upon and optically interacts with the fluid 302, including any analytes thereof. As a result, optically interacted radiation 318 is generated by and reflected from the fluid 302. Those skilled in the art, however, will readily recognize that alternative variations of the optical computing device 306 may allow the optically interacted radiation 318 to be generated by being transmitted, scattered, diffracted, absorbed, emitted, or re-radiated by and/or from the fluid 302 without departing from the scope of the disclosure.

The optically interacted radiation 318 generated by the interaction with the material of interest may be directed to or otherwise received by an ICE 320 arranged within the optical computing device 306. The ICE 320 may be a spectral component substantially similar to the ICE 100 described above with reference to FIG. 1. Accordingly, in operation the ICE 320 may be configured to receive the optically interacted radiation 318 and produce modified electromagnetic radiation 322 corresponding to a particular characteristic of interest. In particular, the modified electromagnetic radiation 322 is electromagnetic radiation that has optically interacted with the ICE 320, whereby an approximate mimicking of the regression vector corresponding to the characteristic of interest is obtained. In some embodiments, the characteristic of interest corresponds to the fluid 302, which encompasses embodiments where the characteristic of interest corresponds to a particular analyte of the fluid 302.

It should be noted that, while FIG. 3B depicts the ICE 320 as receiving reflected electromagnetic radiation from the fluid 302, the ICE 320 may be arranged at any point along the optical train of the optical computing device 306, without departing from the scope of the disclosure. For example, in one or more embodiments, the ICE 320 (as shown in dashed) may be arranged within the optical train prior to the sampling window 316 and equally obtain substantially the same results. In other embodiments, the sampling window 316 may serve a dual purpose as both a transmission window and the ICE 320 (i.e., a spectral component). In yet other embodiments, the ICE 320 may generate the modified electromagnetic radiation 322 through reflection, instead of transmission therethrough.

Moreover, while only one ICE 320 is shown in the optical computing device 306, embodiments are contemplated herein which include the use of at least two ICE components in the optical computing device 306 configured to cooperatively determine the characteristic of interest in the fluid 302. For example, two or more ICE components may be arranged in series or parallel within the optical computing device 306 and configured to receive the optically interacted radiation 318 and thereby enhance sensitivities and detector limits of the optical computing device 306. In other embodiments, two or more ICE may be arranged on a movable assembly, such as a rotating disc or an oscillating linear array, which moves such that the individual ICE components are able to be exposed to or otherwise optically interact with electromagnetic radiation for a distinct brief period of time. The two or more ICE components in any of these embodiments may be configured to be either associated or disassociated with the characteristic of interest in the fluid 302. In other embodiments, the two or more ICE may be configured to be positively or negatively correlated with the characteristic of interest. These optional embodiments employing two or more ICE components are further described in co-pending U.S. patent application Ser. No. 13/456,264 entitled "Methods and Devices for Optically Determining a Characteristic of a Substance," Ser. No. 13/456,405 entitled "Methods and Devices for Optically Determining A Characteristic of a Substance," Ser. No. 13/456,302 entitled "Methods and Devices for Optically Determining A Characteristic of a Substance," and Ser. No. 13/456,327 entitled "Methods and Devices for Optically Determining A Characteristic of a Substance," the contents of which are hereby incorporated by reference in their entireties.

In some embodiments, it may be desirable to monitor more than one characteristic of interest at a time using the optical computing device 306. In such embodiments, various configurations for multiple ICE components can be used, where each ICE component is configured to detect a particular and/or distinct characteristic of interest corresponding, for example, to a fluid, an analyte thereof, or a reagent or a product resulting from a chemical reaction in the fluid. In some embodiments, the characteristic of interest can be analyzed sequentially using multiple ICE components that are provided a single beam of electromagnetic radiation being reflected from or transmitted through the fluid 302. In some embodiments, as briefly mentioned above, multiple ICE components can be arranged on a rotating disc, where the individual ICE components are only exposed to the beam of electromagnetic radiation for a short time. Advantages of this approach can include the ability to analyze multiple characteristics of interest within the fluid 302 using a single optical computing device and the opportunity to assay additional characteristics simply by adding additional ICE components to the rotating disc corresponding to those additional characteristics.

In other embodiments, multiple optical computing devices can be placed at a single location along the flow path, where each optical computing device contains a unique ICE that is configured to detect a particular characteristic of interest. In such embodiments, a beam splitter can divert a portion of the electromagnetic radiation being reflected by, emitted from, or transmitted through the fluid 302 and into each optical computing device. Each optical computing device, in turn, can be coupled to a corresponding detector or detector array that is configured to detect and analyze an output of electromagnetic radiation from the respective optical computing device. Parallel configurations of optical computing devices can be particularly beneficial for applications that require low power inputs and/or no moving parts.

Those skilled in the art will appreciate that any of the foregoing configurations can further be used in combination with a series configuration in any of the present embodiments. For example, two optical computing devices having a rotating disc with a plurality of ICE components arranged thereon can be placed in series for performing an analysis at a single location along the length of the flow path. Likewise, multiple detection stations, each containing optical computing devices in parallel, can be placed in series for performing a similar analysis.

The modified electromagnetic radiation 322 generated by the ICE 320 may subsequently be conveyed to a detector 324 for quantification of the signal. The detector 324 may be any device capable of detecting electromagnetic radiation, and may be generally characterized as an optical transducer. In some embodiments, the detector 324 may be, but is not limited to, a thermal detector such as a thermopile or photoacoustic detector, a semiconductor detector, a piezoelectric detector, a charge coupled device (CCD) detector, a video or array detector, a split detector, a photon detector (such as a photomultiplier tube), photodiodes, combinations thereof, or the like, or other detectors known to those skilled in the art.

In some embodiments, the detector 324 may be configured to produce an output signal 326 in real-time or near real-time in the form of a voltage (or current) that corresponds to the particular characteristic of interest. The voltage returned by the detector 324 is essentially the dot product of the optical interaction of the optically interacted radiation 318 with the respective ICE 320 as a function of the concentration of the characteristic of interest. As such, the output signal 326 produced by the detector 324 and the concentration of the characteristic of interest may be related, for example, directly proportional. In other embodiments, however, the relationship may correspond to a polynomial function, an exponential function, a logarithmic function, and/or a combination thereof.

In some embodiments, the optical computing device 306 may include a second detector 328, which may be similar to the first detector 324 in that it may be any device capable of detecting electromagnetic radiation. Similar to the second detector 216 of FIG. 2, the second detector 328 of FIG. 3 may be used to detect radiating deviations stemming from the electromagnetic radiation source 308. Undesirable radiating deviations can occur in the intensity of the electromagnetic radiation 310 due to a wide variety of reasons and potentially causing various negative effects on the output of the optical computing device 306. These negative effects can be particularly detrimental for measurements taken over a period of time. In some embodiments, radiating deviations can occur as a result of a build-up of film or material on the sampling window 316 which has the effect of reducing the amount and quality of light ultimately reaching the first detector 324. Without proper compensation, such radiating deviations could result in false readings and the output signal 326 would no longer be primarily or accurately related to the characteristic of interest.

To compensate for these types of undesirable effects, the second detector 328 may be configured to generate a compensating signal 330 generally indicative of the radiating deviations of the electromagnetic radiation source 308, and thereby normalize the output signal 326 generated by the first detector 324. As illustrated, the second detector 328 may be configured to receive a portion of the optically interacted radiation 318 via a beamsplitter 332 in order to detect the radiating deviations. In other embodiments, however, the second detector 328 may be arranged to receive electromagnetic radiation from any portion of the optical train in the optical computing device 306 in order to detect the radiating deviations, without departing from the scope of the disclosure.

In some applications, the output signal 326 and the compensating signal 330 may be conveyed to or otherwise received by a signal processor 334 communicably coupled to both the detectors 324,328. The signal processor 334 may be a computer including a non-transitory machine-readable medium, and may be configured to computationally combine the compensating signal 330 with the output signal 326 in order to normalize the output signal 326 in view of any radiating deviations detected by the second detector 328. In some embodiments, computationally combining the output and compensating signals 326,330 may entail computing a ratio of the two signals 326,330. For example, the concentration or magnitude of each characteristic of interest determined using the optical computing device 306 can be fed into an algorithm run by the signal processor 334. The algorithm may be configured to make predictions on how the properties of the fluid 302 change if the concentration of the measured characteristic of interest changes.

In real-time or near real-time, the signal processor 334 may be configured to provide a resulting output signal 336 corresponding to the characteristic of interest, e.g., a concentration of a reagent or resulting product present in the fluid 302. In some embodiments, as briefly discussed above, the resulting output signal 336 may be readable by an operator who can consider the results and make proper adjustments to the flow path or take appropriate action, if needed, based upon the magnitude of the measured characteristic of interest. In some embodiments, the resulting output signal 336 may be conveyed, either wired or wirelessly, to the user for consideration.

Figure 4:
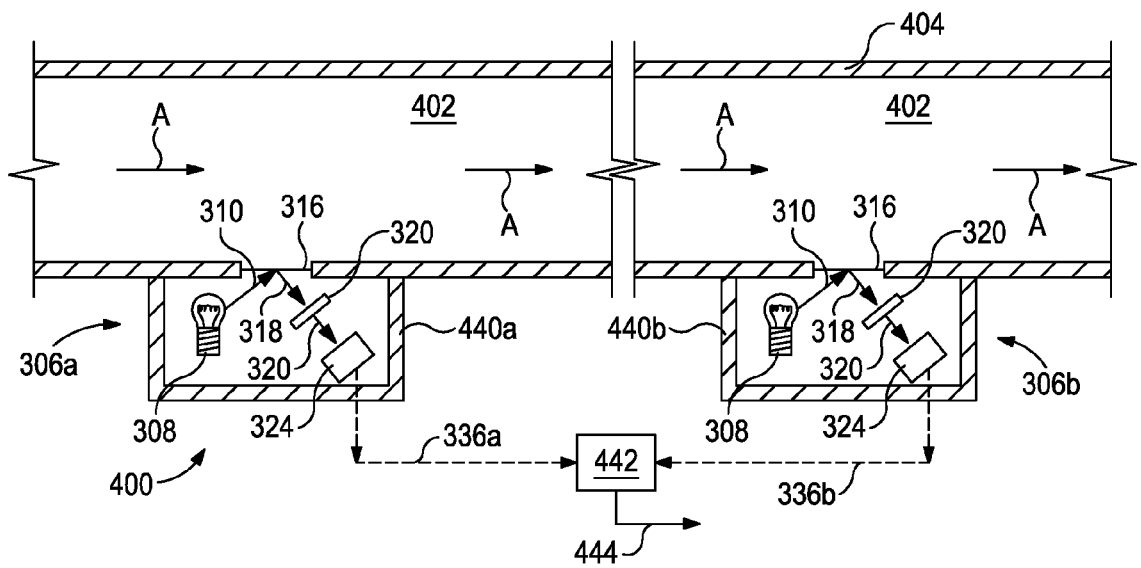
FIG. 4 illustrates an exemplary system for monitoring a material of interest, according to one or more embodiments.

Referring now to FIG. 4, with continued reference to FIGS. 2 and 3A-B, illustrated is another exemplary system 400 for monitoring a fluid 402, according to one or more embodiments. In the illustrated embodiment, the fluid 402 may be contained or otherwise flowing within an exemplary flow path 404. The flow path 404 may be a flow line, a pipeline, or an annulus and the fluid 402 present therein may be flowing in the general direction indicated by the arrows A (i.e., from upstream to downstream). As will be appreciated, however, the flow path 404 may be any other type of flow path or combination of flow paths, as generally described or otherwise defined herein, e.g., a storage container fluidly connected to a pipeline that may optionally be fluidly connected to a mixer or transportation container. As such, portions of the flow path 404 may be independently arranged substantially vertical, substantially horizontal, or any directional configuration therebetween, without departing from the scope of the disclosure.

The system 400 may include at least a first optical computing device 306a and a second optical computing device 306b. The optical computing devices 306a,b may be similar in some respects to the optical computing devices 200, 306 of FIGS. 2 and 3B, respectively, and like numerals indicate like elements that will not be described in detail relative to FIG. 4. As illustrated, the first and second optical computing devices 306a,b may each be associated with the flow path 404 at independent and distinct monitoring locations along the length of the flow path 404. Specifically, the first optical computing device 306a may be located at a first monitoring location along the flow path 404 and the second optical computing device 306b may be located at a second monitoring location along the flow path 404, where the first monitoring location fluidly communicates with the second monitoring location via contiguous portions of the flow path 404. As described in greater detail herein, each optical computing device 306a,b may be useful in determining a particular characteristic of the fluid 402 within the flow path 404, such as determining a characteristic of interest of the fluid 402 at the corresponding location along the flow path 404.

In some embodiments, the second optical computing device 306b is arranged at a predetermined distance from the first optical computing device 306a along the length of the flow path 404. In other embodiments, however, the first optical computing device 306a may be randomly spaced from the second optical computing device 306b, without departing from the scope of the disclosure. For example, the first and second optical computing devices 306a,b may be spaced from each other at two or more random points in a mixer or at two or more random points in a mixing system (e.g., coupled to a mixer container, coupled to a mixing structure like a paddle, and/or couple to an inlet and/or outlet of the mixer container). Moreover, while only two optical computing devices 306a,b are shown in FIG. 4, it will be appreciated that the system 400 may employ more than two optical computing devices in conjunction with the flow path 404, without departing from the scope of the disclosure. In such embodiments, each additional optical computing device may be spaced from the first and second optical computing devices 306a,b at predetermined or random distances, depending on the application.

In some embodiments, each device 306a,b may be housed within an individual housing coupled or otherwise attached to the flow path 404 at its respective location. As illustrated, for example, the first device 306a may be housed within a first housing 440a and the second device 306b may be housed within a second housing 440b. In some embodiments, the first and second housings 440a,b may be mechanically coupled to the flow path 404 using, for example, mechanical fasteners, brazing or welding techniques, adhesives, magnets, combinations thereof or the like. Each housing 440a,b may be configured to substantially protect the internal components of the respective devices 306a,b from damage or contamination from the external environment. Moreover, each housing 440a,b may be designed so as to withstand the pressures that may be experienced within the flow path 404 and thereby provide a fluid tight seal between the flow path 404 and the respective housing 440a,b.

In some embodiments, the detector 324 in each device 306a,b may be configured to produce an output signal in real-time or near real-time in the form of a voltage (or current) that corresponds to the particular characteristic of interest in the fluid 402. For example, the detector 324 arranged within the first device 306a may generate a first output signal 336a, and the detector 324 arranged within the second device 306b may generate a second output signal 336b. The voltage returned by each detector 324 is essentially the dot product of the optical interaction of the optically interacted radiation 318 with the respective ICE 320 as a function of the concentration of the characteristic of interest of the fluid 402.

The output signal 336a,b from each device 306a,b may be conveyed to or otherwise received by a signal processor 442 communicably coupled to the detector 324. The signal processor 442 may be a computer including a non-transitory machine-readable medium, and may employ an algorithm configured to calculate or otherwise determine the differences between the two output signals 336a,b at a single time point or over a plurality of time points (i.e., a difference in the detection history at each location).

For example, the first output signal 336a may be indicative of a characteristic of interest in the fluid 402 (e.g., the concentration of an analyte, a particle size distribution, and the like) at the location of the first device 306a along the flow path 404, and the second output signal 336b may be indicative of the characteristic of interest in the fluid 402 at the location of the second device 306b along the flow path 404. Accordingly, the signal processor 442 may be configured to determine how the characteristic of interest in the fluid 402 has changed between the first and second monitoring locations along the flow path 404. In some embodiments, the algorithm employed by the signal processor 442 may take into account the distance between the two optical computing devices 306a,b so as to probe substantially the same portion of the fluid 402 at two different locations. Depending upon the application, the monitoring distances may be short (e.g., meters or even centimeters), or long (e.g., thousands of miles), mainly depending on the application of interest. For those knowledgeable in the art, they will also appreciate that multiple monitors may be employed at a variety of points along the flow path 404.

In real-time or near real-time, the signal processor 442 may be configured to provide a resulting output signal 444. The output signal 444 may, in some embodiments, be (1) a difference between the characteristic of interest at the location of each optical computing device 306a,b taken at a single time point, (2) a difference between the characteristic of interest for substantially the same portion of the fluid at the location of each optical computing device 306a,b using an algorithm to account for the time and distance of travel, or (3) a difference between the histories (i.e., the detected difference measured over a plurality of time points) of the characteristic of interest at the location of each optical computing device 306a,b (which may optionally be adjusted with an algorithm as described in (2)). For example when using the concentration of an analyte to relate to a reaction, if the history of the characteristic of the analyte is substantially at a steady state over time at two or more locations and the difference between said magnitudes falls within predetermined limits (e.g., corresponding to predetermined limits of the characteristic of interest), the reaction may be progressing as desired with no action needing to be taken. Changes in the magnitude (e.g., spike or a steady increase/decrease) at one or more locations may indicate that corrective action needs to be taken. For example, a steady increase in an analyte concentration may indicate that there is a slow leak between the two locations being compared.

With continued reference to FIG. 4, in some embodiments, the resulting output signal 444 may be conveyed, either wired or wirelessly, to a user for consideration. In other embodiments, the resulting output signal 444 may be recognized by the signal processor 442 as being within or without a predetermined or preprogrammed range of suitable operation. If the resulting output signal 444 or variation thereof exceeds the predetermined or preprogrammed range of operation, the signal processor 442 may be configured to alert the user so appropriate corrective action may be taken, or otherwise autonomously undertake the appropriate corrective action such that the resulting output signal 444 returns to a value falling within the predetermined or preprogrammed range of operation.

Figure 5:
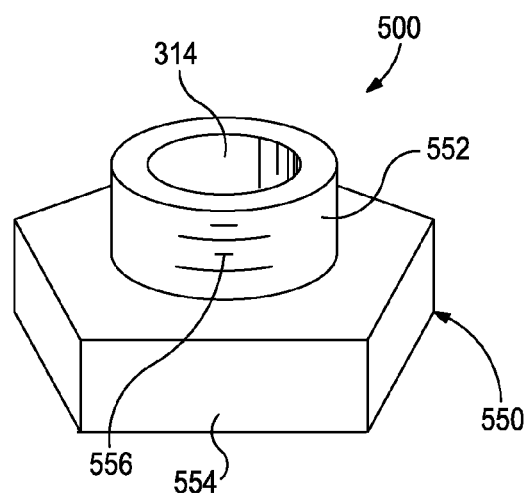
FIG. 5 illustrates an exemplary housing that may be used to house an optical computing device, according to one or more embodiments.

Referring now to FIG. 5, with continued reference to FIGS. 3 and 4, illustrated is an exemplary housing 500 that may be used to house an optical computing device, according to one or more embodiments. The housing 500 may serve the same purpose as the first and second housings 440a and 440b discussed above with reference to FIG. 4 and, in at least one embodiment, may be an alternative embodiment for each housing 440a,b. Those skilled in the art, however, will readily recognize that several alternative designs and configurations of housings used to house the optical computing devices are suitable for the presently disclosed systems and methods. Indeed, the housing embodiments described and disclosed herein are by way of example only, and should not be considered limiting to the exemplary systems and methods disclosed herein.

As illustrated, the housing 500 may be in the general form of a bolt 550 which encloses the various components of an optical computing device, such as one of the first or second optical computing devices 306a,b of FIG. 4. In one embodiment, the components of the optical computing device housed within the housing 500 may be generally housed within a stem 552 of the bolt 550, and the bolt 550 may have a hex head 554 for manual manipulation of the housing 500 using, for example, a wrench or other suitable torque-generating hand tool.

In at least one embodiment, the housing 500 defines external threads 556 that are threadable with corresponding mating pipe threads (not shown) provided in, for example, an opening defined in the casing 304 (FIG. 3) or the flow path 404 (FIG. 4) that is configured to receive the housing 500. The threads 556 may be sealed to the mating pipe threads with a thread sealant in order to help withstand the elevated pressures that may be experienced in the casing 304 or the flow path 404. The sampling window 316 is configured to be in optical communication with the fluid 302 (FIG. 3B), 402 (FIG. 4) and allows optical interaction between the fluid 302, 402 and the other internal components of the internally-housed optical computing device.

It should be noted that embodiments are contemplated herein where a plurality of systems and methods can be designed to monitor and/or analyze cementing operations using the principles disclosed herein.

Figure 6:
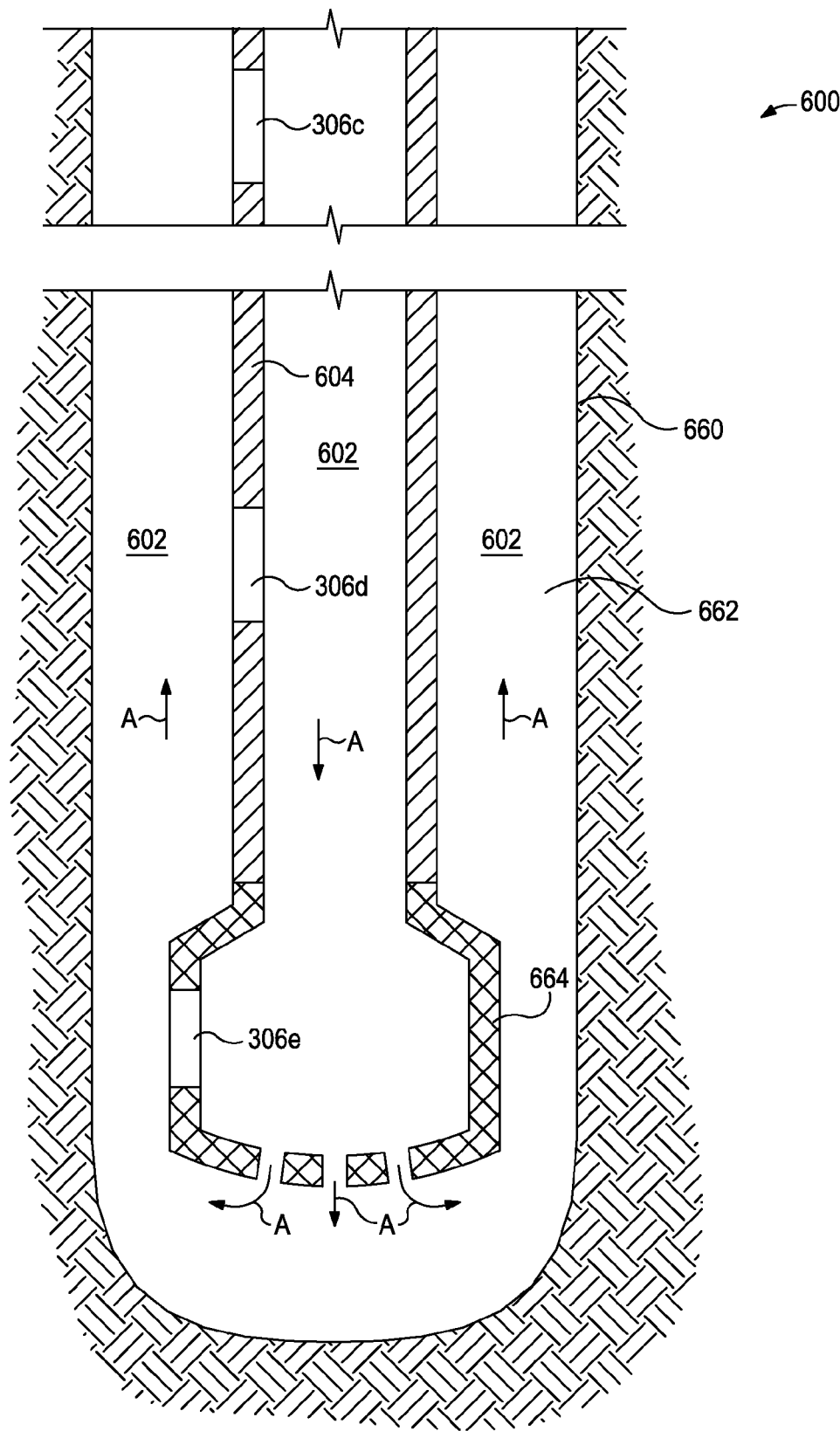
FIG. 6 illustrates an exemplary system for monitoring a material of interest, according to one or more embodiments.

Referring now to FIG. 6, illustrated is another exemplary system 600 for monitoring a fluid 602, which may be useful in monitoring and/or analyzing a chemical reaction process that may occur within the fluid 602, determining the location of the fluid 602, and/or the properties of the fluid 602, according to one or more embodiments. The system 600 may include a plurality of optical computing devices 306c,d,e connected at a plurality of locations to a flow path that includes a casing 604, a casing shoe 664, and an annulus 662 formed between the casing 604 and the wellbore 660. The fluid 602 contained within or otherwise flowing through the flow path may, in some embodiments, be flowing in the general direction indicated by the arrows A (i.e., from upstream to downstream).

The optical computing devices 306c,d,e may be substantially similar to the optical computing devices 200, 306 of FIGS. 2 and 3A-B, respectively, and therefore will not be described in detail relative to FIG. 6. As illustrated, the optical computing devices 306c,d may be coupled to the casing 604 at different locations, and the optical computing device 306e may be coupled to the casing shoe 664. The optical computing devices 306c,d,e may be configured to receive and detect optically interacted light from the fluid 602 within the casing 604, the casing shoe 664, the annulus 662, or any suitable combination thereof (e.g., optical computing device 306e may be configured to receive and detect optically interacted light from the fluid 602 within the casing shoe 664, the annulus 662, or any combination thereof).

Figure 7A:
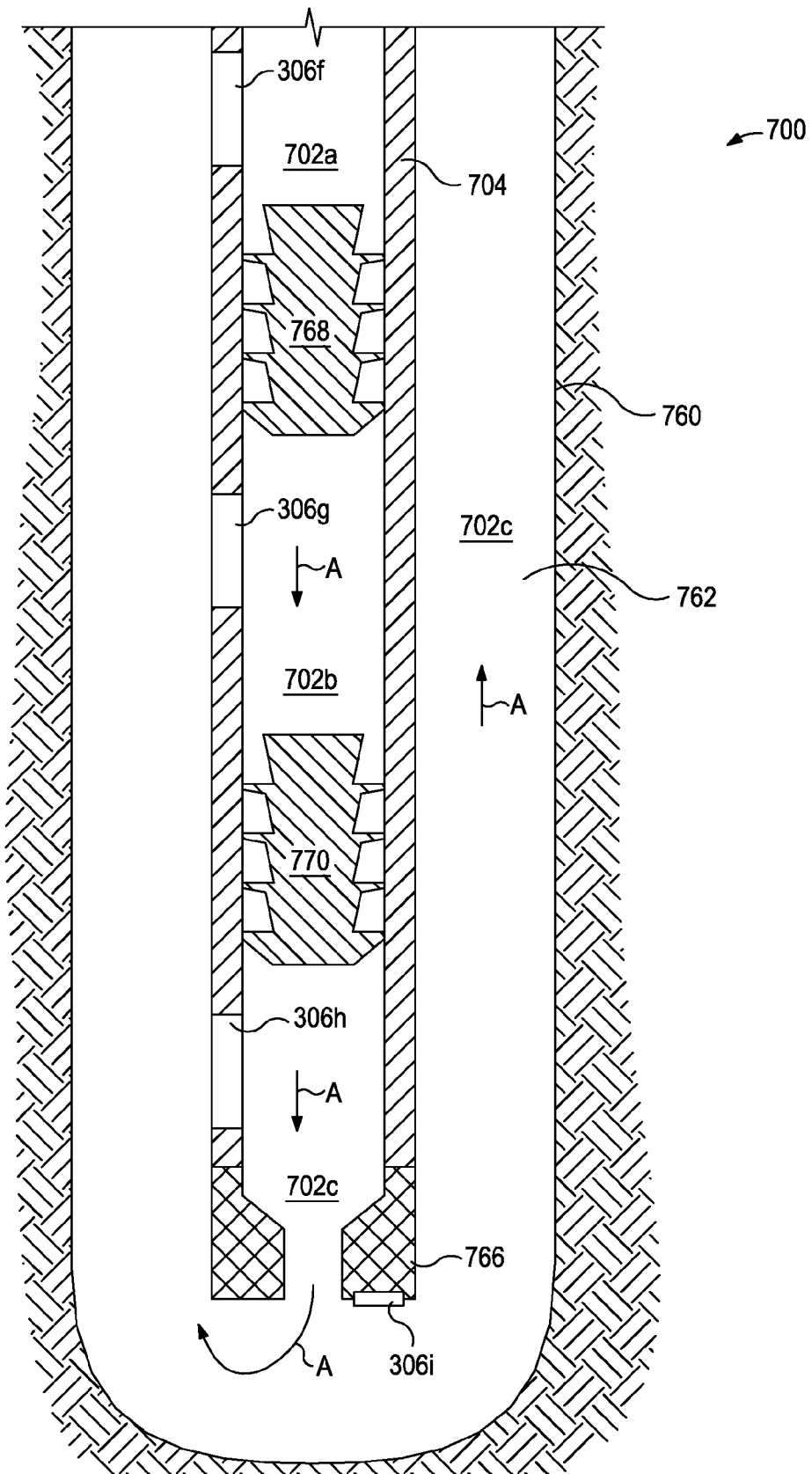
FIGS. 7A-C illustrate an exemplary system for monitoring a material of interest, according to one or more embodiments.

Referring now to FIG. 7A, illustrated is another exemplary system 700 for monitoring a fluid, which may be useful in monitoring and/or analyzing a chemical reaction process that may occur within the fluid, determining the location of the fluid, determining the properties of the fluid, and/or determining the condition of a tool used in conjunction with the fluid, according to one or more embodiments. In the illustrated embodiment, three fluids (shown as a displacement fluid 702a, a cement slurry 702b, and a drilling fluid 702c) may be contained or otherwise flowing through a casing 704 and a wellbore annulus 760 in conjunction with a top cementing plug 768 and a bottom cementing plug 770. In at least one embodiment, the fluids 702a-c present in the exemplary flow path may be flowing in the general direction indicated by the arrows A. As will be appreciated, however, in other embodiments the flow path may be any other type of flow path, as generally described or otherwise defined herein. For example, the flow path may be a pipeline or other conduit and the fluid may not necessarily be flowing while being monitored.

As illustrated in FIG. 7A, with continued reference to FIGS. 3A-B and 4, moving the fluids 702a,b in the direction of arrows A through the casing 704 and the wellbore annulus 762 causes the displacement of the drilling fluid 702c by the bottom cementing plug 770, which includes flexible wipers configured to engage the inner radial surface of the casing 704 and thereby clean the drilling fluid 702c from the walls of the casing 704. In the process, the cement slurry 702b displaces the bottom cementing plug 770 axially downward, which, inter alia, is designed to minimize contamination of the cement slurry 702b with the drilling fluid 702c. The cement slurry 702b is, in turn, displaced by the top cementing plug 768, which also include flexible wipers configured to engage the inner radial surface of the casing 704 and thereby clean the cement slurry 702b from the walls of the casing 704, which, inter alia, mitigates cement setting on the walls of the casing 704. The displacement fluid 702a is used to provide the necessary hydraulic pressure to, inter alia, impel the cementing plugs 768,770 through the casing 704 and the various fluids 702b,702c through the casing 704 and the wellbore annulus 762.

The bottom cementing plug 770 can be configured to prevent fluid flow therethrough during movement through the casing 704 but allow fluid flow therethrough when it reaches the landing collar 766 and a large enough pressure differential causes one or more pressure seals or valves within the bottom cementing plug 770 to burst. Once the one or more pressure seals or valves within the bottom cementing plug 770 burst or otherwise release, fluid flow is facilitated through the bottom cementing plug 770 and into the wellbore annulus 762. Eventually, the top cementing plug 768 may be configured to mate with the bottom cementing plug 770 and seal the flow path through the bottom cementing plug 770.

In the exemplary system 700 illustrated in FIG. 7A, optical computing devices 306f,g,h,i may be arranged in a variety of locations to monitor and analyze the fluids 702a-c at predetermined points within the system 700. For example, optical computing devices 306f,g,h are illustrated as being coupled to the casing 704 in series, which enables, inter alia, the monitoring of at least one characteristic of interest as the fluids 702a,b,c and cementing plugs 768,770 move through the casing 704. Further, exemplary system 700 includes an optical computing device 306i coupled to or otherwise arranged on the landing collar 766, which may enable monitoring of at least one characteristic of interest as the fluids 702b,c flow from the casing 704 to the annulus 762.

Figure 7B:
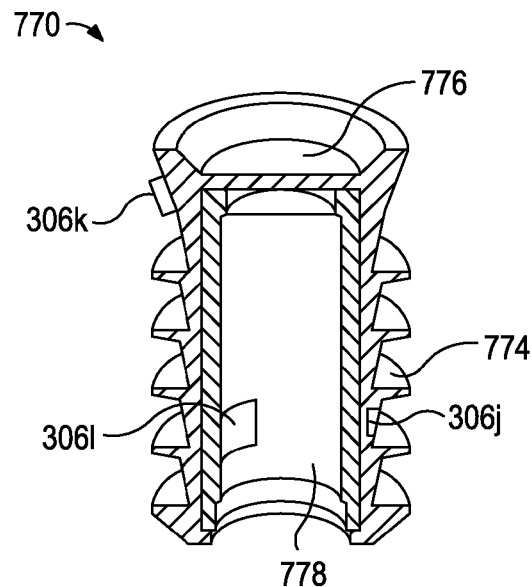

Referring now to FIG. 7B, with continued reference to FIGS. 3A-B, 4, and 7A, a plurality of optical computing devices 306j,306k,306l may be coupled to or otherwise arranged on the bottom cementing plug 770. For instance, the optical computing device 306j is illustrated as being disposed between two flexible wipers 774, and the optical computing device 306k is illustrated as being disposed above the flexible wipers 774. In exemplary operation, the optical computing devices 306j,k may be configured to detect drilling fluid 702c (FIG. 7A) or cement slurry 702b (FIG. 7A) leakage past corresponding individual flexible wipers 774, thereby providing an indication of the overall efficacy and/or failure of the individual flexible wipers 774. The optical computing device 306l is depicted as being arranged on an inner radial surface of the bottom cementing plug 770. In exemplary operation, after the one or more pressure seals or valves (i.e., a pressure mechanism 776) within the bottom cementing plug 770 burst or otherwise release, the device 306l may be useful in detecting and analyzing the cement slurry 702b as it flows through a plug flow path 778 defined within the bottom cementing plug 770. In at least one embodiment, the optical computing device 306l may be useful in, inter alia, determining if the pressure mechanism 776 has been properly triggered and providing an analysis of the properties of the cement slurry 702b as it passes through the plug flow path 778. As some pressure mechanisms include pressure sensitive valves, the optical computing device 306l may be configured to provide real time or near-real time analysis to identify the fluid in the plug flow path 778, thereby indicating if the operational parameters need to be changed, like running pressure, which may be adjusted at the surface, when desired, to levels that close the pressure sensitive mechanism 776.

Figure 7C:
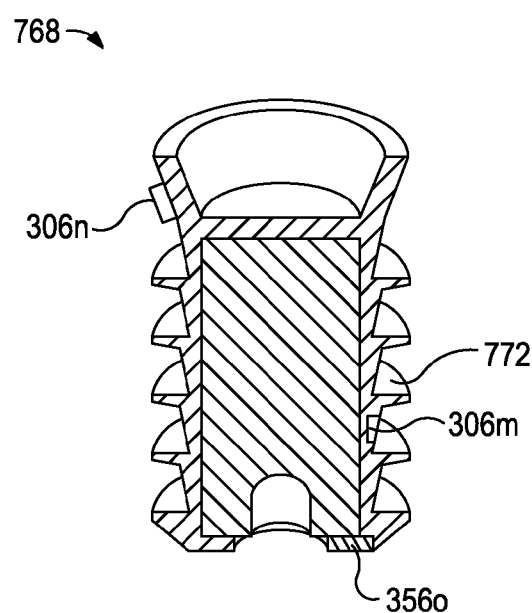

Referring now to FIG. 7C, with continued reference to FIGS. 3A-B, 4, and 7A-B, the top cementing plug 768 may have a plurality of optical computing devices 306m,306n, 306o arranged or otherwise disposed thereon. The optical computing device 306m is illustrated as being disposed between two flexible wipers 772, which has similar functionality as the optical computing device 306j of FIG. 7B. The optical computing device 306n is illustrated as being disposed above the flexible wipers 772, and may exhibit similar functionality as the optical computing device 306k of FIG. 7B. The optical computing device 306o is illustrated as being arranged on the top cementing plug 768 such that it will be in contact with the cement slurry 702b (FIG. 7A). As a result, the optical computing device 306o may be useful in, inter alia, monitoring in real-time the properties of the cement slurry 702b while in the casing 704, thereby providing an opportunity for adjustments of the operation parameters based on changes in the properties of the cement slurry 702b. For example, in some instances, if the cement setting process proceeds more quickly than expected, perhaps due to contamination or higher wellbore temperatures than anticipated, operation parameters like running speed may be increased to place the cement slurry 702b more quickly. In other instances, for example, if the cement setting process appears to be proceeding more slowly than expected, the subsequent steps that allow time for the cement slurry 702b to set may be extended.

Figure 8:
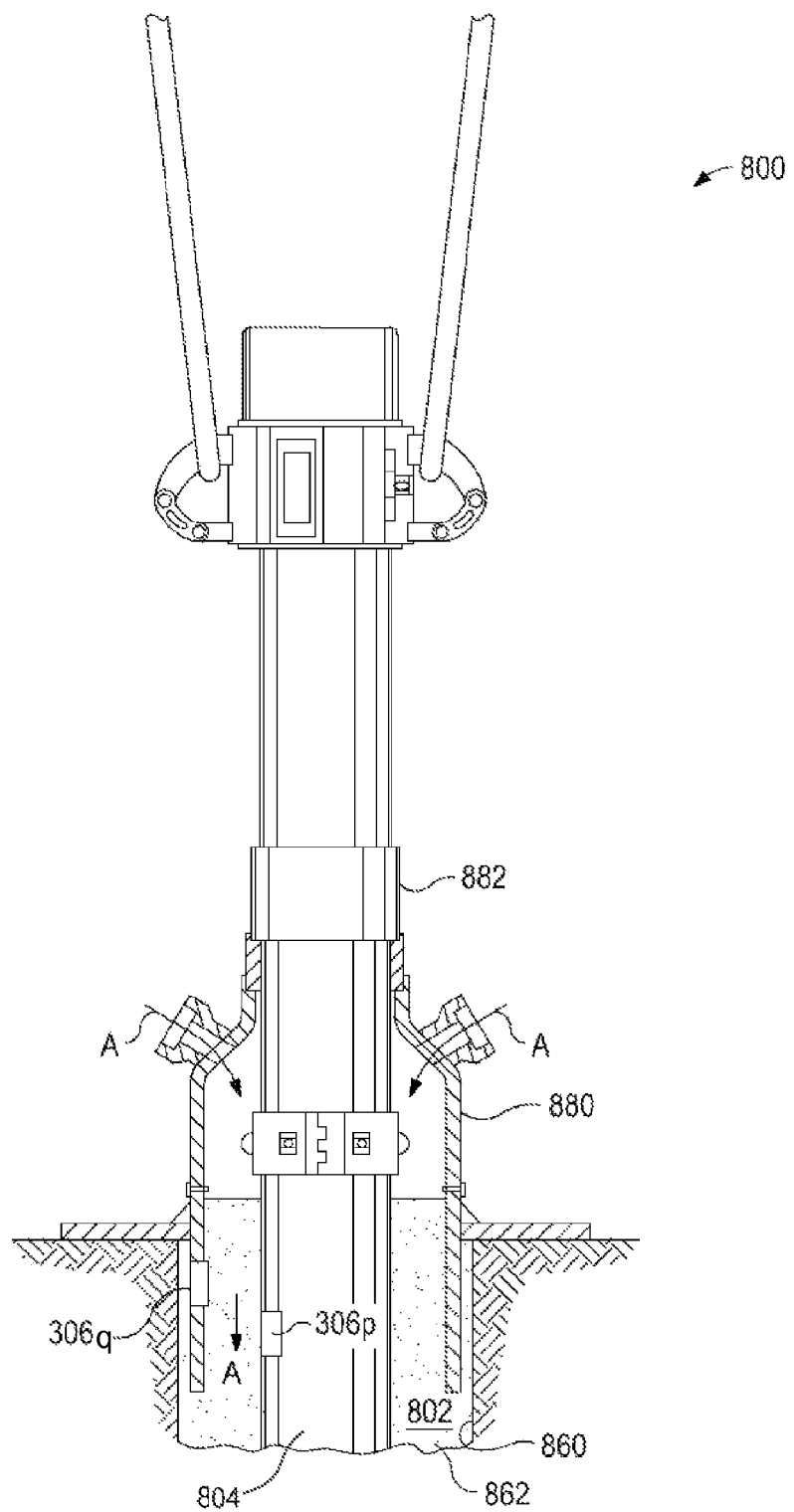
FIG. 8 illustrates an exemplary system for monitoring a material of interest, according to one or more embodiments.

Referring now to FIG. 8, with continued reference to FIGS. 3A-B and 4, illustrated is another exemplary system 800 for monitoring a fluid 802, which may be useful in monitoring and/or analyzing a characteristic of interest described herein, determining the location of the fluid 802, determining the properties of the fluid 802, and/or determining the condition of a tool used in conjunction with the fluid 802, according to one or more embodiments. In particular, the embodiments disclosed with respect to the system 800 may be useful in downhole reverse cementing operations. In the illustrated embodiment, a flow path may be defined through a surface pack-off device 880 and a fluidly coupled annulus 862. In at least one embodiment, the fluid 802 present in the exemplary flow path may be flowing in the general direction indicated by the arrows A. The system 800 may include a plurality of optical computing devices 306p,q, where the optical computing device 306p is coupled to or otherwise arranged on a casing 804 and the optical computing device 306q is coupled to or otherwise arranged on the surface pack-off device 880. Further, in the illustrated embodiment, a smart hanger 882 may include a signal processor, not shown, that is capable of receiving output signals (e.g., wirelessly or with other physical communication) from the optical computing devices 306p,q and providing a resultant output signal similar to the output signal 444 of FIG. 4.

One skilled in the art would recognize the applicability of a smart hanger that comprises a signal processor that could be coupled to a plurality of optical computing devices that are, in turn, coupled to, for example, a casing, a cementing plug, a casing shoe, a collar (e.g., a float collar, a casing collar, a or landing collar), and the like, and any combination thereof.

Figure 9:
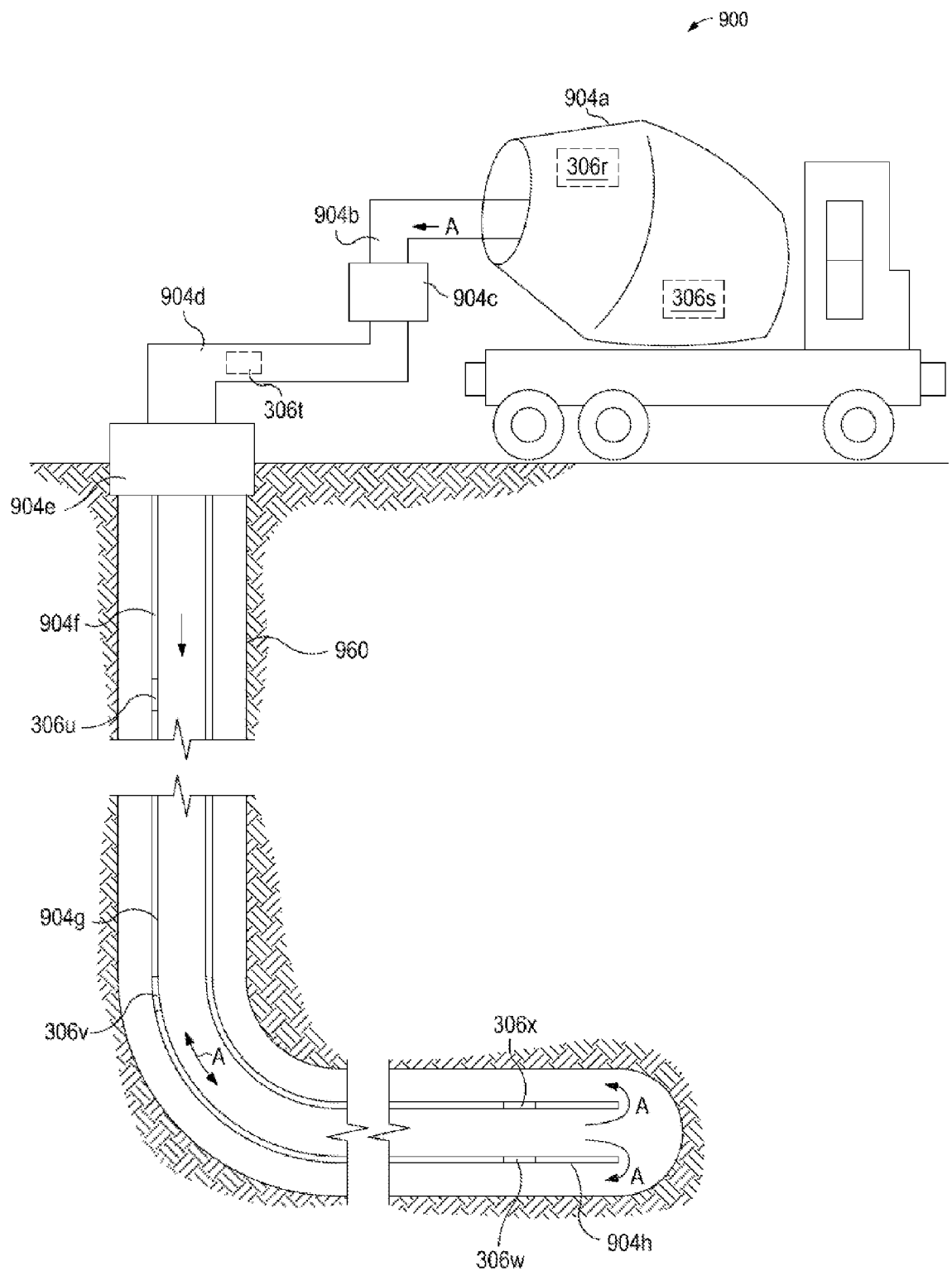
FIG. 9 illustrates an exemplary system for monitoring a material of interest, according to one or more embodiments.

Referring now to FIG. 9, with continued reference to FIGS. 3A-B and 4, illustrated is another exemplary system 900 for monitoring a fluid, which may be useful in monitoring and/or analyzing a characteristic of interest described herein, determining the location of the fluid, determining the properties of the fluid, and/or determining the condition of a tool used in conjunction with the fluid, according to one or more embodiments. The exemplary system 900 may have a flow path 904 (shown as sections 904a,b,c,d,e,f,g,h) with a plurality of optical computing devices 306r,s,t,u,v,w,x strategically arranged along the flow path 904 at a variety of predetermined locations, according to one or more embodiments. Extensively integrated systems like the exemplary system 900 may be useful in determining the overall quality of a cementing operation at almost every point in the process. For instance, the system 900 may be configured to monitor and/or analyze the fluid while mixing a dry cement blend with water, pumping the resultant cement slurry, allowing the cement slurry to set, and any other facet of the cementing operation where an optical computing device 306 may be arranged. As will be appreciated, by determining the various characteristics of interest (e.g., those relating to specific analytes, reactions, or fluid properties), one may be able to determine the quality or efficacy of the various processes.

In the illustrated embodiment, the flow path 904 includes sections 904a,b,c,d,e,f,g,h which correspond to a mixer 904a of a truck, a first section of a pipe 904b, a pump 904c, a second section of a pipe 904d, a wellhead 904e, a first casing section 904f, a second casing section 904g, and a third casing section 904h. The fluid present in the flow path 904 may be flowing in the general direction indicated by the arrows A (i.e., from upstream to downstream). As noted above, however, the flow path 904 may be any other type of flow path or combination of flow paths, as generally described or otherwise defined herein, e.g., a storage container fluidly connected to a pipeline that may optionally be fluidly connected to the mixer 904a or other transportation container.

A plurality of optical computing devices 306r,s,t,u,v,w,x may be disposed along the flow path 904 so as to interact with the fluid at predetermined or strategic locations. The system 900 may be useful in some embodiments for analyzing or otherwise monitoring the process of mixing a dry cement blend with water in the mixer 904a to yield a cement slurry and introducing the cement slurry into a wellbore 960.

In some embodiments, the optical computing devices 306r,s may be useful in determining when the dry cement blend within the mixer 904a is substantially homogeneous (e.g., by analyzing a particle size distribution or analyte concentration during mixing and comparing the corresponding output signals either as a difference between locations where substantially no difference may indicate homogeneity or as change over a plurality of time points where a plateau may indicate homogeneity). Once a substantially homogenous dry cement blend is achieved or otherwise detected by the devices 306r,s, water may be added and mixed with the dry cement blend to yield a cement slurry. The optical computing devices 306r,s may be useful in determining when the cement slurry is ready for introduction into the wellbore 960 (e.g., by detecting at a plurality of time points for a hydration level, slurry density, and/or water-to-cement ratio, and comparing respective output signals for a plateau or minimum value reached). Depending on the characteristics of interest of the dry cement blend and the cement slurry, the optical computing devices 306r,s may be configured to measure more than one characteristic of interest. By measuring at two locations and optionally at a plurality of time points (i.e., over a predetermined time period), a more accurate determination of the dry cement blend homogeneity and hydration level may be obtained.

Once ready, the cement slurry may be pumped through the flow path 904 with the use of the pump 904c and travel from the mixer 904a through the pipe sections 904b,d and into the wellhead 904e where it is conveyed to the casing sections 904f,g,h. The optical computing devices 306t,u,v,w,x arranged along the flow path 904 may be utilized as described in previous examples for independently analyzing one or more characteristics of interest. As illustrated, the optical computing devices 306w,x may be arranged on the third casing section 904h at about the same depth, but disposed at different radial points about the circumference of the third casing section 904h (e.g., internal circumference, external circumference, or both). Such a configuration may be especially advantageous in deviated wellbores to analyze for changes in the properties of the fluid about the same portion of the casing, but at varying radial configurations. For example, differences in a particle size distribution within the third casing section 904h may be an indication of the settling of cement particulates therein, which could adversely affect the mechanical properties of the resultant set cement.

Systems similar to the system 900 of FIG. 9 may be useful in the quality control of cementing operations. For example, if the dry cement blend is not adequately mixed before water introduction, portions of the cement slurry may undergo premature setting while the set time of other portions of the cement slurry may be longer than anticipated. Further, ensuring proper hydration and slurry density of the cement slurry before introduction into the wellbore may, in some embodiments, ensure the proper set time and/or implementation of set-time retarders or accelerators, which in turn provides for an efficient cementing operation and mitigates costs associated with nonproductive time and remedial operations.

Some embodiments of the present invention may involve containing and/or flowing a fluid or a series of fluids (i.e., two or more fluids in series) into a flow path or a series of flow path sections; optically interacting light from an electromagnetic radiation source with the fluid and at least one integrated computational element, thereby generating optically interacting light; receiving with at least one detector the optically interacted light; and generating with the at least one detector an output signal corresponding to a characteristic of the fluid. In some embodiments, the steps of optically interacting light and generating an output signal may occur at more than one location, and the output signal may be correlated to the corresponding location. In some embodiments, the step of optically interacting light may occur at a plurality of time points over a predetermined period of time, thereby generating a corresponding plurality of output signals. In some embodiments, a hybrid thereof is envisioned thereby producing more than one plurality of output signals, each plurality of output signals corresponding to a specific location within a flow path.

Comparison of (e.g., taking a difference between) at least two output signals may provide information about the characteristic of interest over a specific distance within the flow path, and consequently information about a property of the fluid. For example, comparing output signals from spaced optical computing devices within a flow path may provide data on a chemical reaction occurring within the flow path, and whether the particular reaction is occurring as planned or whether any alterations to the process need to be initiated.

The systems and methods provided herein for analyzing a characteristic of a fluid may be utilized in conjunction with a plurality of cementing operations. For clarity in describing various embodiments of cementing operation methods herein, the term "analyzing a characteristic of interest," and the like, refers to any of the corresponding methods described herein (including multiple location and multiple time point embodiments) that utilize any optical computing devices described herein.

Some embodiments of performing a cementing operation may involve at least one of the following steps (not necessarily in the order listed), where each step may optionally include analyzing a characteristic of interest and may optionally include analyzing the same and/or different characteristic of interest as compared to any other step in the method:

containing a fluid in a flow path or series of flow path sections described herein;
flowing a fluid in a flow path or series of flow path sections described herein;
mixing a fluid in a flow path or series of flow path sections described herein;
transferring a fluid from a first flow path or flow path section to a second flow path or flow path section;
introducing a fluid into a wellbore or a flow path defined within the wellbore (e.g., a casing, an annulus, a flow path defined within a tool, and the like);
adding an analyte described herein to a cement fluid composition;
adding an analyte described herein to a cement fluid composition in response to a change in the characteristic of interest;
adding an analyte described herein to a cement fluid composition in response to the characteristic of interest reaching a substantially steady-state and/or a desired level or magnitude;
adding an analyte described herein to a cement fluid composition in response to the characteristic of interest falling outside a predetermined set of limits; and
changing an operational parameter;
changing an operation parameter in response to a change in the characteristic of interest;
changing an operational parameter in response to the characteristic of interest reaching a substantially steady-state and/or a desired level or magnitude;
changing an operational parameter in response to the characteristic of interest falling outside a predetermined set of limits; and
moving a tool (e.g., a cementing plug or a surface pack-off device) through a wellbore (which encompasses a flow path therein);
analyzing the integrity and/or efficacy of a tool based on the characteristic of interest;
allowing a cement slurry to set within a wellbore or flow path contained therein;
performing a remedial operation;
performing a remedial operation in response to a change in the characteristic of interest;
performing a remedial operation in response to the characteristic of interest falling outside a predetermined set of limits; and
any combination thereof.

It should also be noted that the various drawings provided herein are not necessarily drawn to scale nor are they, strictly speaking, depicted as optically correct as understood by those skilled in optics. Instead, the drawings are merely illustrative in nature and used generally herein in order to supplement understanding of the systems and methods provided herein. Indeed, while the drawings may not be optically accurate, the conceptual interpretations depicted therein accurately reflect the exemplary nature of the various embodiments disclosed.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The invention claimed is:

1. A method comprising:
   containing a cement fluid composition in a flow path comprising a wellbore; and
   optically interacting the cement fluid composition with an integrated computational element having layers with different refractive indices that represent a regression vector related to a characteristic of the cement fluid composition, thereby generating an output signal corresponding to the characteristic of the cement fluid composition, the integrated computational element being coupled to a tool.

2. The method of claim 1, wherein the tool is selected from the group consisting of a cementing plug and a surface pack-off device.

3. The method of claim 1, wherein the flow path further comprises a mixer in fluid communication with the wellbore, wherein the cement fluid composition is a cement slurry produced in the mixer, and wherein the method further comprises optically interacting the cement fluid composition with a second integrated computational element, thereby generating a second output signal corresponding to a second characteristic of the cement fluid composition, the second integrated computational element being coupled to the mixer.

4. The method of claim 1 further comprising:
   communicating the output signal to a hanger.

5. The method of claim 1, wherein the characteristic of the cement fluid composition is at least one selected from the group consisting of chemical composition, impurity content, pH, viscosity, density, ionic strength, total dissolved solids, salt content, porosity, opacity, bacteria content, particle size distribution, color, temperature, hydration level, and an analyte oxidation state.

6. The method of claim 1 further comprising:
   analyzing an integrity of the tool based on the characteristic of the cement fluid composition.

7. The method of claim 1 further comprising:
   analyzing an efficacy of the tool based on the characteristic of the cement fluid composition.

8. The method of claim 1, wherein the output signal is a dot product of electromagnetic radiation having interacted with the cement fluid composition and the regression vector.

9. A system comprising:
   a cementing plug arranged within a wellbore and in contact with one or more fluids; and
   at least one optical computing device arranged on the cementing plug for monitoring the one or more fluids, the at least one optical computing device having at least one integrated computational element with layers with different refractive indices that represent a regression vector related to a characteristic of the one or more fluids and being configured to optically interact with the one or more fluids and thereby generate optically interacted light, and at least one detector arranged to receive the optically interacted light and generate an output signal corresponding to the characteristic of the one or more fluids.

10. The system of claim 9, wherein the one or more fluids comprise at least one selected from the group consisting of a cement fluid composition, a drilling fluid, a spacer fluid, and a displacement fluid.

11. The system of claim 9, wherein the at least one optical computing device is disposed between two flexible wipers of the cementing plug.

12. The system of claim 9, wherein the cementing plug provides a plurality of wipers and the at least one optical computing device is arranged on the cementing plug either above or below the plurality of wipers.

13. The system of claim 9, wherein the cementing plug defines a plug flow path, the at least one optical computing device being disposed in the plug flow path.

14. The system of claim 9 further comprising:
   a hanger communicably coupled to the at least one optical computing device and configured to receive the output signal.

15. The system of claim 14, wherein the hanger comprises a signal processor.

16. The system of claim 14, wherein the hanger is communicably coupled to at least one second optical computing device to receive a second output signal corresponding to the characteristic of the one or more fluids, the at least one second optical computing device not being coupled to the cementing plug.

17. The system of claim 9, wherein the output signal is a dot product of electromagnetic radiation having interacted with the one or more fluids and the regression vector.

* * * * *